(12) United States Patent
Pathak et al.

(10) Patent No.: US 8,535,705 B2
(45) Date of Patent: Sep. 17, 2013

(54) BIOCOMPATIBLE POLYMERS AND HYDROGELS AND METHODS OF USE

(75) Inventors: Chandrashekhar P. Pathak, Austin, TX (US); Amarpreet S. Sawhney, Lexington, MA (US); Peter G. Edelman, Franklin, MA (US)

(73) Assignee: Incept, LLC, Lexington, MA (US)

( * ) Notice: Subject to any disclaimer, the term of this patent is extended or adjusted under 35 U.S.C. 154(b) by 1705 days.

(21) Appl. No.: 11/985,588

(22) Filed: Nov. 16, 2007

(65) Prior Publication Data
US 2008/0095736 A1 Apr. 24, 2008

Related U.S. Application Data

(60) Division of application No. 10/373,269, filed on Feb. 24, 2003, now abandoned, which is a continuation of application No. 09/454,900, filed on Dec. 3, 1999, now Pat. No. 6,566,406.

(60) Provisional application No. 60/110,849, filed on Dec. 4, 1998.

(51) Int. Cl.
*A61F 2/00* (2006.01)

(52) U.S. Cl.
USPC .......................................................... 424/426

(58) Field of Classification Search
None
See application file for complete search history.

(56) References Cited

U.S. PATENT DOCUMENTS

| | | |
|---|---|---|
| 2,533,004 A | 12/1950 | Ferry et al. |
| 3,520,949 A | 7/1970 | Shepard et al. |
| 4,101,380 A | 7/1978 | Rubenstein et al. |
| 4,359,049 A | 11/1982 | Redl et al. |
| 4,414,976 A | 11/1983 | Schwarz et al. |
| 4,427,651 A | 1/1984 | Stroetmann |
| 4,565,784 A | 1/1986 | Franzblau et al. |
| 4,601,286 A | 7/1986 | Kaufman |
| 4,631,055 A | 12/1986 | Redl et al. |
| 4,631,188 A | 12/1986 | Stoy et al. |
| 4,646,730 A | 3/1987 | Schonfeld et al. |

(Continued)

FOREIGN PATENT DOCUMENTS

| | | |
|---|---|---|
| EP | 0246380 A2 | 10/1986 |
| EP | 0414848 B1 | 1/1990 |

(Continued)

OTHER PUBLICATIONS

Jarrett et al., "Bioabsorbable Hydrogel Tissue Barrier: In Situ Gelation Kinetics," Soc. for Biomater., Transactions of 21st Annual Meeting: 182 (1995).

(Continued)

*Primary Examiner* — Paul Dickinson
(74) *Attorney, Agent, or Firm* — Dardi & Herbert, PLLC.; Curtis B. Herbert

(57) ABSTRACT

Biocompatible crosslinked polymers, and methods for their preparation and use, are disclosed in which the biocompatible crosslinked polymers are formed from water soluble precursors having electrophilic and nucleophilic groups capable of reacting and crosslinking in situ. Methods for making the resulting biocompatible crosslinked polymers biodegradable or not are provided, as are methods for controlling the rate of degradation. The crosslinking reactions may be carried out in situ on organs or tissues or outside the body. Applications for such biocompatible crosslinked polymers and their precursors include controlled delivery of drugs, prevention of postoperative adhesions, coating of medical devices such as vascular grafts, wound dressings and surgical sealants.

18 Claims, 10 Drawing Sheets

(56) References Cited

U.S. PATENT DOCUMENTS

| | | |
|---|---|---|
| 4,693,887 A | 9/1987 | Shah |
| 4,717,378 A | 1/1988 | Perrault et al. |
| 4,735,616 A | 4/1988 | Eibl et al. |
| 4,740,534 A | 4/1988 | Matsuda et al. |
| 4,803,075 A | 2/1989 | Wallace et al. |
| 4,826,945 A | 5/1989 | Cohn et al. |
| 4,874,368 A | 10/1989 | Miller et al. |
| 4,902,281 A | 2/1990 | Avoy |
| 4,925,677 A | 5/1990 | Feijen |
| 4,932,942 A | 6/1990 | Maslanka |
| 4,937,270 A | 6/1990 | Hamilton et al. |
| 4,938,763 A | 7/1990 | Dunn et al. |
| 4,978,336 A | 12/1990 | Capozzi et al. |
| 4,979,959 A | 12/1990 | Guire |
| 5,030,215 A | 7/1991 | Morse et al. |
| 5,041,292 A | 8/1991 | Feijen |
| 5,093,319 A | 3/1992 | Higham et al. |
| 5,100,992 A | 3/1992 | Cohn et al. |
| 5,104,909 A | 4/1992 | Grasel et al. |
| 5,116,315 A | 5/1992 | Capozzi et al. |
| 5,143,662 A | 9/1992 | Chesterfield et al. |
| 5,160,745 A | 11/1992 | DeLuca et al. |
| 5,162,430 A | 11/1992 | Rhee et al. |
| 5,192,743 A | 3/1993 | Hsu et al. |
| 5,213,760 A | 5/1993 | Dziabo, Jr. et al. |
| 5,213,808 A | 5/1993 | Bar-Shalom et al. |
| 5,219,564 A | 6/1993 | Zalipsky et al. |
| 5,278,202 A | 1/1994 | Dunn et al. |
| 5,281,662 A | 1/1994 | Ito et al. |
| 5,290,776 A | 3/1994 | Caulkett et al. |
| 5,292,362 A | 3/1994 | Bass et al. |
| 5,296,518 A | 3/1994 | Grasel et al. |
| 5,304,595 A | 4/1994 | Rhee et al. |
| 5,318,524 A | 6/1994 | Morse et al. |
| 5,324,775 A | 6/1994 | Rhee et al. |
| 5,328,955 A | 7/1994 | Rhee et al. |
| 5,330,768 A | 7/1994 | Park et al. |
| 5,368,563 A | 11/1994 | Lonneman et al. |
| 5,395,923 A | 3/1995 | Bui-Khac et al. |
| 5,399,351 A | 3/1995 | Leshchiner et al. |
| 5,405,607 A | 4/1995 | Epstein |
| 5,410,016 A | 4/1995 | Hubbell et al. |
| 5,413,791 A | 5/1995 | Rhee et al. |
| 5,419,491 A | 5/1995 | Breitsprecher |
| 5,423,821 A | 6/1995 | Pasque |
| 5,426,148 A | 6/1995 | Tucker |
| 5,431,639 A | 7/1995 | Shaw |
| 5,446,090 A | 8/1995 | Harris |
| 5,446,091 A | 8/1995 | Rhee et al. |
| 5,455,027 A | 10/1995 | Zalipsky et al. |
| 5,470,911 A | 11/1995 | Rhee et al. |
| 5,474,540 A | 12/1995 | Miller et al. |
| 5,475,052 A | 12/1995 | Rhee et al. |
| 5,476,909 A | 12/1995 | Kim et al. |
| 5,505,704 A | 4/1996 | Pawelka et al. |
| 5,514,379 A | 5/1996 | Weissleder et al. |
| 5,514,380 A | 5/1996 | Song et al. |
| 5,527,856 A | 6/1996 | Rhee et al. |
| 5,529,914 A | 6/1996 | Hubbell et al. |
| 5,550,187 A | 8/1996 | Rhee et al. |
| 5,550,188 A | 8/1996 | Rhee et al. |
| 5,565,519 A | 10/1996 | Rhee et al. |
| 5,567,435 A | 10/1996 | Hubbell et al. |
| 5,573,934 A | 11/1996 | Hubbell et al. |
| 5,580,923 A | 12/1996 | Yeung et al. |
| 5,583,114 A | 12/1996 | Barrows et al. |
| 5,587,175 A | 12/1996 | Viegas et al. |
| 5,605,541 A | 2/1997 | Holm |
| 5,605,938 A | 2/1997 | Roufa et al. |
| 5,612,052 A | 3/1997 | Shalaby |
| 5,614,587 A | 3/1997 | Rhee et al. |
| 5,618,563 A | 4/1997 | Berde et al. |
| 5,626,863 A | 5/1997 | Hubbell et al. |
| 5,631,322 A | 5/1997 | Veronese et al. |
| 5,643,464 A | 7/1997 | Rhee et al. |
| 5,645,583 A | 7/1997 | Villain et al. |
| 5,656,035 A | 8/1997 | Avoy |
| 5,668,236 A | 9/1997 | Engelhardt et al. |
| 5,672,622 A | 9/1997 | Hedgepeth et al. |
| 5,681,576 A | 10/1997 | Henry |
| 5,698,213 A | 12/1997 | Jamiolkowski et al. |
| 5,702,361 A | 12/1997 | Evans et al. |
| 5,714,159 A | 2/1998 | Shalaby |
| 5,733,950 A | 3/1998 | Dunn et al. |
| 5,741,223 A | 4/1998 | Janzen et al. |
| 5,744,545 A | 4/1998 | Rhee et al. |
| 5,749,968 A | 5/1998 | Melanson et al. |
| 5,752,974 A | 5/1998 | Rhee et al. |
| 5,773,025 A | 6/1998 | Baichwal |
| 5,776,493 A | 7/1998 | Barclay et al. |
| 5,786,421 A | 7/1998 | Rhee et al. |
| 5,800,541 A | 9/1998 | Rhee et al. |
| 5,801,033 A | 9/1998 | Hubbell et al. |
| 5,807,581 A | 9/1998 | Rosenblatt et al. |
| 5,810,885 A | 9/1998 | Zinger |
| 5,814,621 A | 9/1998 | Kanaya et al. |
| 5,830,178 A | 11/1998 | Jones et al. |
| 5,830,196 A | 11/1998 | Hicks |
| 5,844,023 A | 12/1998 | Tomka |
| 5,858,746 A | 1/1999 | Hubbell et al. |
| 5,863,551 A | 1/1999 | Woerly |
| 5,869,096 A | 2/1999 | Barclay et al. |
| 5,874,500 A * | 2/1999 | Rhee et al. .................. 525/54.1 |
| 5,900,245 A | 5/1999 | Sawhney et al. |
| 5,932,462 A | 8/1999 | Harris et al. |
| 5,936,035 A | 8/1999 | Rhee et al. |
| 5,962,023 A | 10/1999 | Jamiolkowski et al. |
| 5,986,043 A | 11/1999 | Hubbell et al. |
| 5,990,193 A | 11/1999 | Russell et al. |
| 6,017,301 A | 1/2000 | Schwartz et al. |
| 6,020,326 A | 2/2000 | Roufa et al. |
| 6,033,654 A | 3/2000 | Stedronsky et al. |
| 6,051,248 A | 4/2000 | Sawhney et al. |
| 6,051,648 A | 4/2000 | Rhee et al. |
| 6,110,484 A | 8/2000 | Sierra |
| 6,124,273 A | 9/2000 | Drohan et al. |
| 6,129,761 A | 10/2000 | Hubbell |
| 6,133,325 A | 10/2000 | Schwartz et al. |
| 6,136,333 A | 10/2000 | Cohn et al. |
| 6,149,931 A | 11/2000 | Schwartz et al. |
| 6,153,211 A | 11/2000 | Hubbell et al. |
| 6,156,345 A | 12/2000 | Chudzik et al. |
| 6,156,531 A | 12/2000 | Pathak et al. |
| 6,162,241 A | 12/2000 | Coury et al. |
| 6,165,489 A | 12/2000 | Berg et al. |
| 6,166,130 A | 12/2000 | Rhee et al. |
| 6,174,645 B1 | 1/2001 | Russell et al. |
| 6,177,095 B1 | 1/2001 | Sawhney et al. |
| 6,201,065 B1 | 3/2001 | Pathak et al. |
| 6,214,966 B1 | 4/2001 | Harris |
| 6,238,403 B1 | 5/2001 | Greene, Jr. et al. |
| 6,251,382 B1 | 6/2001 | Greenwald et al. |
| 6,258,351 B1 | 7/2001 | Harris |
| 6,261,544 B1 | 7/2001 | Coury et al. |
| 6,271,278 B1 | 8/2001 | Park et al. |
| 6,277,394 B1 | 8/2001 | Sierra |
| 6,303,102 B1 | 10/2001 | Schlichte |
| 6,306,922 B1 | 10/2001 | Hubbell et al. |
| 6,312,725 B1 | 11/2001 | Wallace et al. |
| 6,323,278 B2 | 11/2001 | Rhee et al. |
| 6,348,558 B1 | 2/2002 | Harris et al. |
| 6,371,975 B2 | 4/2002 | Cruise et al. |
| 6,413,539 B1 | 7/2002 | Shalaby |
| 6,428,571 B1 | 8/2002 | Lentz et al. |
| 6,458,147 B1 | 10/2002 | Cruise et al. |
| 6,458,889 B1 | 10/2002 | Trollsas et al. |
| 6,465,001 B1 | 10/2002 | Hubbell et al. |
| 6,495,127 B1 | 12/2002 | Wallace et al. |
| 6,515,534 B2 | 2/2003 | Dabral |
| 6,566,406 B1 | 5/2003 | Pathak et al. |
| 6,610,033 B1 | 8/2003 | Melanson et al. |
| 6,632,457 B1 | 10/2003 | Sawhney |
| 6,818,018 B1 | 11/2004 | Sawhney |
| 6,958,212 B1 | 10/2005 | Hubbell et al. |

| | | |
|---|---|---|
| 7,009,034 B2 | 3/2006 | Pathak et al. |
| 7,332,566 B2 | 2/2008 | Pathak et al. |
| 2001/0003126 A1 | 6/2001 | Rhee et al. |
| 2004/0076602 A1 | 4/2004 | Harris |
| 2008/0287633 A1* | 11/2008 | Drumheller .................. 526/348 |

FOREIGN PATENT DOCUMENTS

| | | |
|---|---|---|
| EP | 0732109 A1 | 9/1996 |
| EP | 0863933 B1 | 11/1996 |
| EP | 1 967 220 A2 | 9/2008 |
| JP | 3-502704 | 6/1991 |
| JP | 5-508161 | 11/1993 |
| JP | 6-508169 | 9/1994 |
| JP | 10-503102 | 3/1998 |
| WO | 89/02445 A1 | 3/1989 |
| WO | WO 91/09641 A1 | 7/1991 |
| WO | 92/00105 A1 | 1/1992 |
| WO | 92/20349 A1 | 11/1992 |
| WO | 96/03159 A1 | 2/1996 |
| WO | WO 96/03159 A1 | 2/1996 |
| WO | WO 96/14095 A1 | 5/1996 |
| WO | 9719973 A1 | 6/1997 |
| WO | WO 97/22371 A1 | 6/1997 |
| WO | WO 97/22372 A1 | 6/1997 |
| WO | WO 98/35631 A1 | 8/1998 |
| WO | 99/03454 A1 | 1/1999 |
| WO | 9908718 A3 | 2/1999 |
| WO | WO 99/10022 | 3/1999 |
| WO | WO 99/14259 | 3/1999 |
| WO | WO 99/22770 A1 | 5/1999 |
| WO | WO 99/34833 C2 | 7/1999 |
| WO | 0009087 A1 | 2/2000 |
| WO | 0033764 A1 | 6/2000 |
| WO | 0168155 A1 | 9/2001 |
| WO | WO 01/66017 | 9/2001 |

OTHER PUBLICATIONS

Pathak et al., U.S. File History, U.S. Appl. No. 10/373,269, filed Feb. 24, 2003.
Pathak et al., U.S. File History, U.S. Appl. No. 10/373,939, filed Feb. 25, 2003.
Achterberg et al., "Hydroactive Dressings and Serum Proteins: An in Vitro Study," *J Wound Care*, 5:79-82 (1996)(abstract).
Baines et al., "Adsorption and Removal of Protein Bound to Hydrogel Contact Lenses," *Optom Vis Sci*, 67:807-810 (1990) (abstract).
Bick, "Hemostasis Defects," *Seminars in Thrombosis and Hemostasis*, 11:263-264 (1985).
Bick, "Physiology and Pathophysiology of Hemostasis During Cardiac Surgery" (excerpts).
Bite et al., "Macrosorb Kieselguhr-Agarose Composite Adsorbents. New Tools for Downstream Process Design and Scale Up. Scientific Note," *Appl. Biochem Biotechnol*, 18:275-284 (1988) (abstract).
Burczak et al, "Protein Permeation Through Poly(Vinyl Alcohol) Hydrogel Membranes," *Biomaterials*, 15:231-238 (1994) (abstract).
Burgi, "A Simple Method for the Concentration of Protein for Electrophoresis of Urine and Cerebrospinal Fluid," *Z Klin Chem Klin Biochem*, 5:277 (1967) (abstract).
Gander et al., "Crosslinked Poly(alkylene Oxides) for the Preparation of Controlled Release Micromatrices", *Journal of Controlled Release*, (5)271-283 (1988).
Garrett et al., "Human Serum Albumin Adsorption on Hydrogel Contact Lenses in Vitro," *Invest aphthalmol Vis Sci*, 37:2594-2602 (1996).
Hill-West et al., "Prevention of Postoperative Adhesions in the Rat by in Situ Photopolymerization of Bioresorbably Hydrogel Barriers," *Obstetrics and Gynecology*, 83(1): 59 (1994).
Irwin et al., "The Effect of Cyclodextrins on the Stability of Peptides in Nasal Enzymic Systems," *Pharmaceutical Research*, 11:1968:1703 (1994).
Keller et al., "Determination of the Protein Concentration in the Cerebrospinal Fluid. Criticism of the Methods," *Med Welt*, 23:1319-1325 (1969) (abstract).
Keogh et al., "Albumin Binding Surfaces for Biomaterials", *J. Laboratory & Clinical Med.*, 124.4:537-545 (1994).

Kissell et al., "Parenteral depot-systems on the basis of biodegradable polyesters," *Journal of Controlled Release*, 16:27-42 (1991).
Kluge et al, "Results of Comparisons of Various Methods of Detennining Total Cerebrospinal Fluid Protein," *Dtsch Gesundheitsw*, 23:2039-2041 (1968) (abstract).
Kolthammer, "The in Vitro Adsorption of Drugs from Horse Serum onto Carbon Coated with an Acrylic Hydrogel," *J Pharm Pharmacol*, 27:801-805 (1975) (abstract).
Kulik et al., "In Vitro Platelet Adhesion to Nonionic and Ionic Hydrogels with Different Water Contents," *J. Biomed Mater Res*, 30:295-304 (1996) (abstract).
Lazarus et al., "Selective in Vivo Removal of Rheumatoid Factor by an Extracorporeal Treatment Device in Rheumatoid Arthritis Patients," *Transfusion*, 31:122-128 (1991) (abstract).
Lin et al., "The Influence of Adsorption of Native and Modified Antibodies on Their Activity," *J. Immunol Methods*, 125:67-77 (1989) (abstract).
Mathiowitz et al., "Polyanhydride Microspheres as Drug Carriers I. Hot-Melt Microencapsulation", *J. Controlled Release*, 5:13-22 (1987).
Nihant et al., "Polylactide Microparticles Prepared by Double Emulsion-Evaporation", *J. Colloid & Interface Science*, 173:55-65 (1995).
Pathak et al., "Rapid Photopolymerization of Immunoprotective gels in Contact with Cells and Tissue," *J. Am. Chem. Soc.*, 114:8311-8312 (1992).
Reddi et al, "Polyurethane Microspheres as Drug Carriers", *Macromolecular Reports*, A32:789-799 (1995).
Saraydin et al., "Adsorption of Bovine Serum Albumin onto Acrylamide-Maleic Acid Hydrogels," *Biomaterials*, 15:917-920 (1994) (abstract).
Sawhney et al., "Bioerodible Hydrogels Base don Photopholmerized Poly(ethylene glycol)-co-poly($\alpha$-hydroxy acid) Diacrylate Macromers", *Macromolecules*, 26:581-587 (1993).
Schlag et al., "Fribin Sealant in Orthopedic Surgery" *Fibrin Sealant in Operative Orthopedic Surgery*, vol. 1-7:269-284 (1986).
Sierra, "Fibrin Sealant Adhesive Systems: A Review of Their Chemistry, Material Properties and Clinical Applications," *Journal of Biomaterials Applications*, 7:309-352 (1993).
Silver et al., "Effect of Protein Adsorption on the Blood-Contacting Response of Sulphonated Polyurethanes," *Biomaterials*, 14:834-844 (1993) (abstract).
Smith et al., "Thrombin and Albumin Adsorption to PV A and Heparin-PV A Hydrogels. 2: Competition and Displacement," *J Biomed Mater Res*, 27:89-95 (1993) (abstract).
Tabata et al., "Controlled Delivery Systems for Proteins Using Polyanhydride Microspheres" *Pharmaceutical Research*, 10:487-496 (1993).
Vermes, "Cerebrospinal Fluid Proteins: I. Comparative Study of Concentration Methods," *Arq Neuropsiquiatr*, 41:1-8 (1983) (abstract).
Walther et al., "Pore-Size Distributions of Cationic Polyacrylamide Hydrogels of Different Compositions Maintained at the Same Swelling Capacity", *J. Macromol. Sci.-Phys.* B33 (3&4):267-286 (1994).
Wang et al., "Hydrogels as Separation Agents," *Advances in Polymer Science*, 110:67-79 (1993).
Audebert Md, "Initial Bordeaux Experience with SprayGel Adhesion Barrier System", Presented at the 10th Congress of the European Society for Gynaecological Endoscopy, Nov. 21-24, 2001, Lisbon, Portugal.
Brochure information related to Matrix published by Confluent Surgical, Inc., 2009.
Dunn et al., "Evaluation of a Sprayable Postsurgical Adhesion Barrier in Two Rodent Models", Presented at the Global Congress of Gynecological Endoscopy, 29th Annual Meeting American Association of Gynecological Laparocopists, Nov. 15-19, 2000, Orlando, Florida.
Dunn et al., "Evaluation of the SprayGelTM adhesion barrier in the rat cecum abrasion and rabbit uterine horn adhesion models", Fertility and Sterility, 75(2):411-416, Feb. 2001.
Dunn et al., "Rat (Abdominal) & Rabbit (Pelvic) Studies", Confluent Surgical Inc. Efficacy Preclinical Studies, Summary of the SprayGel Preclinical Animal Models and Studies (2000).

Ferland et al., "Evaluation of a Sprayable, Absorbable Adhesion Barrier in a New Porcine Adhesion Model", Presented at the Global Congress of Gynecological Endoscopy, 29th Annual Meeting American Association of Gynecological Laparocopists, Nov. 15-19, 2000, Orlando, Florida.

Ferland et al., "Evaluation of a sprayable polyethylene glycol adhesion barrier in a porcine efficacy model", Human Reproduction, 16(12): 2718-2723 (2001).

Ferland et al., "Evaluation of SprayGelTM Adhesion Barrier System as a Barrier for the Prevention of Adhesion Formation After Gynecological Surgery", ISGE 10, Chicago, Illinois, Mar. 2001.

Ferland et al., "Porcine (Pelvic) Efficacy Studies", Confluent Surgical Inc. Efficacy Preclinical Studies, Summary of the SprayGel Preclinical Animal Models and Studies (2000).

Jacobs et al, "SprayGelTM as New Intraperitoneal Adhesion Prevention Method for Use in Laparoscopy and Laparotomy", ISGE 10 Convention, Chicago, Illinois, Mar. 2001.

Jacobs et al., "A Pressure-Balanced Sprayer for Intraabdominal Application of Soluble Biomaterials in Laparoscopy", ISGE 10 Convention, Chicago, Illinois, Mar. 2001.

Mettler et al., "Prospective Clinical Trial of SprayGel as a Barrier to Adhesion Formation: Interim Analysis", The Journal of the American Association of Gynecologic Laparocopists, 10(3):339-344 (2003).

Mettler Md et al., A Randomised Prospective Multi-Centre Clinical Trial of Spraygel as a Barrier for Prevention of Adhesion Formation after Gynaecological Surgery: An Intermin Analysis, Presented at the 10th Congress of the European Society for Gynaecol Endoscopy, Nov. 21-24, 2001, Lisbon, Portugal.

Nasaduke et al., "The Use of Autogenous Rabbit Fibrin Sealant to Plug Retinal Holes in Experimental Detachments" Annals of Ophthalmology, 18:324-327 (1986).

Quinn et al., "Biocompatible, glucose-permeablehydrogel for in situ coating of implantable biosensors", Biomaterials, 18(24):1665-1670 (1997).

Sawhney et al. "Rabbit (Pericardial) Adhesion Study", Confluent Surgical Inc. Efficacy Preclinical Studies, Summary of the SprayGel Preclinical Animal Models and Studies (2000).

US 6,214,374, 04/2001, Schmirler et al. (withdrawn)

* cited by examiner

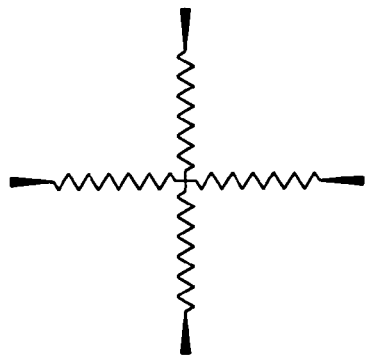
*FIG. 3M*
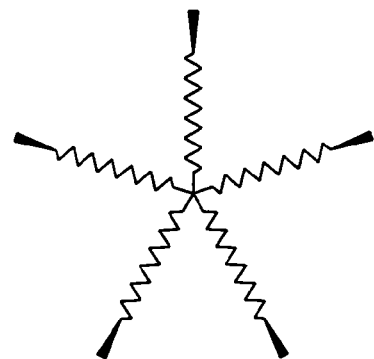
*FIG. 3O*
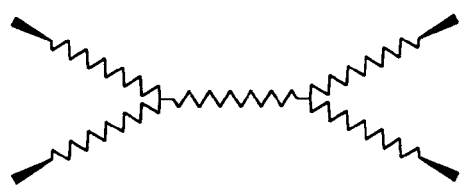
*FIG. 3N*
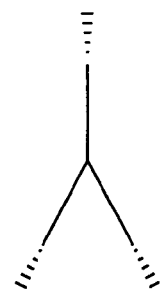
*FIG. 4Q*
*FIG. 4P*
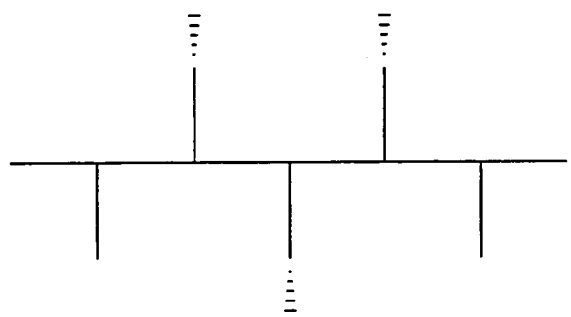
*FIG. 4T*

BIOCOMPATIBLE POLYMERS AND HYDROGELS AND METHODS OF USE

REFERENCE TO RELATED APPLICATION

This application is a divisional of U.S. patent application Ser. No. 10/373,269, filed Feb. 24, 2003 now abandoned, which is a continuation of U.S. patent application Ser. No. 09/454,900, filed Dec. 3, 1999 now U.S. Pat. No. 6,566,406, which claims priority to U.S. patent application Ser. No. 60/110,849, filed Dec. 4, 1998, which patent applications are hereby incorporated by reference herein.

FIELD OF THE INVENTION

The invention relates generally to biocompatible crosslinked polymers, methods for preparing and using same.

BACKGROUND OF THE INVENTION

In the field of medicine there has been a growing recognition of the benefits of using biocompatible crosslinked polymers for the treatment of local diseases. Local diseases are diseases that are manifested at local sites within the living animal or human body, for example atherosclerosis, postoperative adhesions, rheumatoid arthritis, cancer, and diabetes. Biocompatible crosslinked polymers may be used in drug and surgical treatments of such diseases.

Historically, many local diseases have been treated by systemic administration of drugs. In this approach, in order to achieve therapeutic levels of drugs at local disease sites, drugs are delivered (via oral administration or injection) at a high systemic concentration, often with adverse side effects. As an alternative, biocompatible crosslinked polymers may be used as carriers to deliver drugs to local sites within the body, thereby reducing the need for the systemic administration of high concentrations of drugs, while enhancing effectiveness.

Local diseases also have been treated with surgery. Many of these surgical procedures employ devices within the body. These devices may often be formed from or coated with biocompatible crosslinked polymers. For example, a surgical sealant is a device formed from biocompatible crosslinked polymers that may be used to reduce migration of fluid from or into a tissue. For surgical sealants, as with many other surgical procedures, it is sometimes necessary to leave devices in the body after surgery to provide a continuing therapeutic benefit. In such cases, it may be desired that the implant biodegrade over time, eliminating the need for a second surgical procedure to remove the implant after its usefulness has ended. Regardless of whether the implant biodegrades over time, it may also be used, as described above, to deliver drugs to local sites within the body.

Many surgical procedures are now performed in a minimally invasive fashion that reduces morbidity associated with the procedure. Minimally invasive surgery ("MIS") encompasses laparoscopic, thoracoscopic, arthroscopic, intraluminal endoscopic, endovascular, interventional radiological, catheter-based cardiac (such as balloon angioplasty), and like techniques. These procedures allow mechanical access to the interior of the body with the least possible perturbation of the patient's body. Biocompatible crosslinked polymers may be advantageously used to form or coat many of these MIS tools. These polymers may also be used to form sutures, surgical clips, staples, sealants, tissue coatings, implants and drug delivery systems.

Most of the polymers used with MIS applications are preformed to a specific shape before being used in a given application. However, such pre-formed objects have limitations in MIS procedures because they, like other large objects, are difficult to transport through the small access sites afforded by MIS techniques. In addition, the shape of the pre-formed object may not be appropriate because the target tissues where such objects are likely to be used have a variety of shapes and sizes. To overcome these limitations, in situ curable or gelable biocompatible crosslinked polymer systems have been explored. The precursors of such systems are usually liquid in nature. These liquids are then transported to the target tissue and applied on the target organ or tissue. The liquid flows and conforms to the shape of the target organ. The shape of the conformed liquid is then preserved by polymerization or a gelation reaction. This approach has several advantages, including conformity to organ shapes and the ability to implant large quantities of liquid using MIS procedures.

One use of in situ curable biocompatible crosslinked polymers in MIS procedures is to form tissue coatings so as to prevent post-surgical adhesions. For example, J. L. Hill-West et al., "Prevention of Postoperative Adhesions in the Rat by In Situ Photopolymerization of Bioresorbable Hydrogel Barriers," *Obstetrics and Gynecology,* 83(1):59 (1994) describes the use of free radical photopolymerizable water-soluble monomers to form biocompatible crosslinked polymers and thereby prevent post-operative adhesions in two animal models. U.S. Pat. No. 5,410,016 to Hubbell et al. describes the use of free radical photopolymerizable monomers to form biocompatible crosslinked polymers, which then are used as tissue adhesives, controlled-release carriers and as tissue coatings for the prevention of post-operative adhesions.

Free Radical Polymerization

Many of the biocompatible crosslinked polymers previously known used free radical polymerization of vinylic or acrylic functionalities. For example, the Hill-West article describes the use of free radical photopolymerizable, water soluble monomers consisting of 8000 molecular weight ("MW") polyethylene glycol ("PEG") extended at both ends with oligomers of lactic acid and further acrylated at both ends. The aforementioned Hubbell patent describes the use of acetophenone derivative or eosin initiated free radical polymerization of acrylic functionalities of water-soluble biodegradable macromolecules. U.S. Pat. No. 4,938,763 to Dunn describes the use of benzoyl peroxide initiated free radical polymerization of liquid prepolymers.

While free radical polymerization is useful for polymer synthesis, several considerations limit its suitability for use in the living animal or human body. First, the initiator which generates free radicals normally produces several small molecules with known or unknown toxicity. For example, one of the most commonly used photoinitiators, 2,2-dimethoxy 2-phenylacetophenone, generates methyl benzoate and other small compounds during the initiation step. The safety of these initiator fragments must be established before there can be widespread use of such systems for human or animal use. Second, free radicals are extremely reactive species and have life times ranging from 0.01 to 1 second during a typical free radical polymerization reaction. Third, the free radical polymerization, once initiated, is often uncontrollable, frequently producing polymers with high molecular weight and broad molecular weight distribution. Fourth, the most common functionalities used in free radical polymerization are vinylic or acrylic, and the vinyl/acrylic polymers produced by these compositions do not degrade inside the body. Fifth, free radical polymerizable monomers often need to be inhibited with a small amount of inhibitor to prevent the premature polymerization of vinyl functionality. The most commonly used inhibitors are phenols (for example, hydroquinone), which are toxic and hence can be used in only limited amounts, increasing the probability of premature polymerization and crosslinking. Finally, free radical polymerization is often exothermic, and the heat it generates may cause localized burn injuries.

Electrophilic-Nucleophilic Polymerization

Other crosslinked polymers have been formed using electrophilic-nucleophilic polymerization of polymers equipped with either electrophilic or nucleophilic functional groups. For example, U.S. Pat. Nos. 5,296,518 and 5,104,909 to Grasel et al. describe the formation of crosslinked polymers from ethylene oxide rich prepolymers, wherein a polyisocyanate or low molecular weight diisocyanate is used as the electrophilic polymer or crosslinker, and a polyoxyethylene based polyol with in situ generated amine groups is used as the nucleophilic precursor. U.S. Pat. No. 5,514,379 to Weissleder et al. describes the formation of biocompatible crosslinked polymers using polymeric precursors, including polyethylene glycol derivatives, each having multiple electrophilic or nucleophilic functional groups. U.S. Pat. No. 5,426,148 to Tucker describes sealant compositions based on an electrophilic-nucleophilic polymerization reaction between polyether acetoacetylate and polyether amine precursors. U.S. Pat. Nos. 5,874,500 and 5,527,856 to Rhee et al. also describe biocompatible crosslinked polymers, formed from electrophilic-nucleophilic polymerization of polymers having multiple electrophilic or nucleophilic functionalities.

While these electrophilic-nucleophilic polymerization methods do not suffer from the same limitations as free radical polymerization methods, described above, they have other limitations stemming from their use of polymeric precursors. Mixing can be a significant impediment to such reactions since polymeric precursors are often of a higher viscosity and diffusion is impeded, especially with the onset of gelation. Thus, imperfections in the crosslinked structures and weaknesses may result.

In contrast, the use of at least one small molecule precursor (where small molecule refers to a molecule that is not a polymer and is typically of a molecular weight less than 2000 Daltons, or else is a polymer and is of a molecular weight of less than 1000 Daltons) allows for diffusion of the small molecule throughout the crosslinked structure, even after gelation, and thus may result in superior materials. This approach has heretofore been limited to small molecules having electrophilic end groups such as aldehyde. For example, BioGlue, marketed by Cryolife Inc., uses a glutaraldehyde-based electrophilic small molecule to react with a polymeric albumin-based nucleophilic polymer.

However, the small molecule electrophile approaches that are known suffer from several limitations. For example, glutaraldehyde is known to be a toxic compound, and in fact is used to sterilize tissues and can cause significant tissue toxicity. For isocyanate-based approaches, in order for in situ polymerization to occur without local tissue toxicity, other crosslinkers are needed. Moreover, the prior art is silent on the subject of biodegradability of these networks. This is important because in many applications it is important that the materials absorb and be cleared from the body after having served their purpose.

Visualization

As described above, advances in modern surgery provide access to the deepest internal organs with minimally invasive surgical devices. As also described above, biocompatible crosslinked polymers that can be formed in situ are useful in such surgical procedures. However, most such formulations, for example, fibrin glue, are colorless, and the amount of material used is typically very small, leading to a film thickness of only about 0.05 to 1 mm. The resulting colorless solution or film is therefore difficult to visualize, especially in the typically wet and moist surgical environment. Under laparoscopic conditions, visibility is even more difficult due to the fact that only a two-dimensional view of the surgical field is available on the monitor that is used in such procedures.

The use of color in biocompatible crosslinked polymers and precursors may therefore greatly improve their utility in a surgical environment, especially under minimally invasive surgical procedures. Moreover, the better visibility available with the use of color also permits efficient use of materials with minimum wastage.

There thus exists a need for biocompatible crosslinked polymers that can be formed without using free radical chemistry, that can be formed from at least one small molecule precursor that has minimal tissue toxicity, that may be biodegradable, and that may be colored.

SUMMARY OF THE INVENTION

It is therefore an object of the present invention to provide biocompatible crosslinked polymers and methods for their preparation and use, in which the biocompatible crosslinked polymers are formed without using free radical chemistry, and are formed using at least one non-toxic small molecule precursor.

It is another object of this invention to provide such biocompatible crosslinked polymers and methods for their preparation and use, in which the biocompatible crosslinked polymers are formed from aqueous solutions, preferably under physiological conditions.

It is still another object of this invention to provide such biocompatible crosslinked polymers and methods for their preparation and use, in which the biocompatible crosslinked polymers are formed in vivo.

It is a still further object of this invention to provide such biocompatible crosslinked polymers and methods for their preparation and use, in which the biocompatible crosslinked polymers are biodegradable.

Another object of this invention is to provide such biocompatible crosslinked polymers and methods for their preparation and use, in which the biocompatible crosslinked polymers, their precursors, or both are colored.

Another object of this invention is to provide methods for preparing tissue conforming, biocompatible crosslinked polymers in a desirable form, size and shape.

Another object of this invention is to provide methods for using biocompatible crosslinked polymers to form medically useful devices or implants for use as surgical adhesion prevention barriers, as implantable wound dressings, as scaffolds for cellular growth for tissue engineering, or as surgical tissue adhesives or sealants.

Another object of this invention is to provide methods for using biocompatible crosslinked polymers to form medically useful devices or implants that can release bioactive compounds in a controlled manner for local, systemic, or targeted drug delivery.

Another object of this invention is to provide methods and compositions for producing composite biomaterials comprising fibers or particulates made of biodegradable biocompatible crosslinked polymers.

DETAILED DESCRIPTION OF THE INVENTION

Figure 1A:
FIG. 1 depicts electrophilic water soluble and biodegradable crosslinkers or functional polymers, which can be crosslinked with appropriate nucleophilic precursors.
Figure 1B:
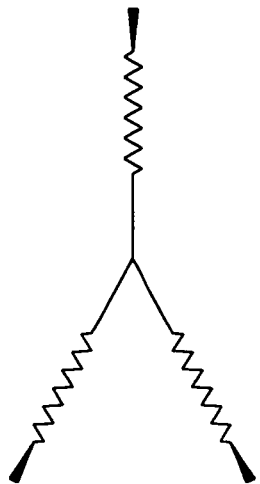
Figure 1C:
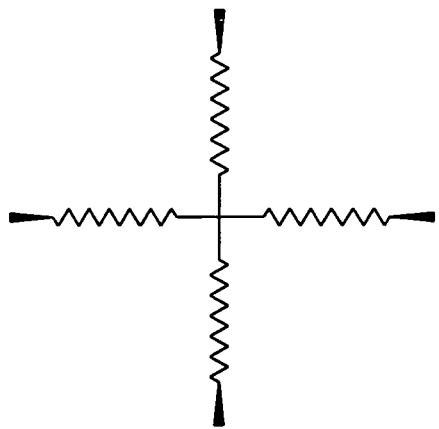
Figure 1E:
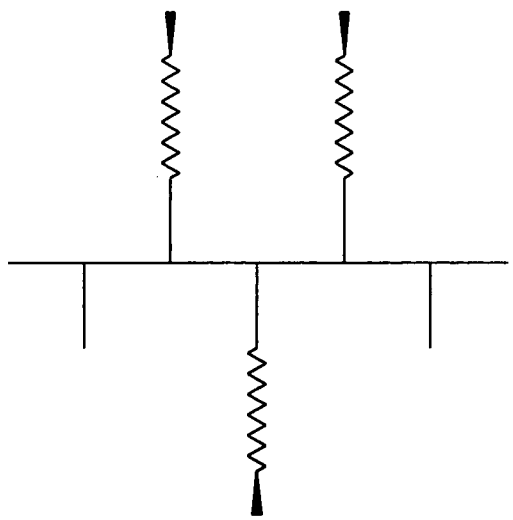
Figure 1D:
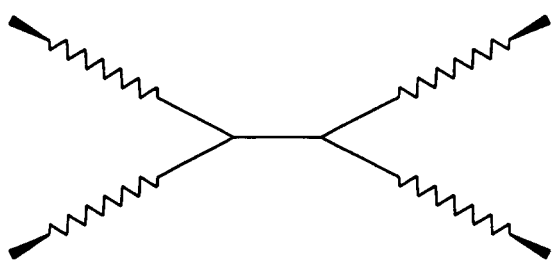
Figure 2F:
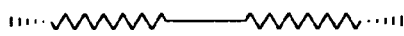
FIG. 2 depicts nucleophilic water soluble and biodegradable crosslinkers or functional polymers, which can be crosslinked with appropriate electrophilic precursors.
Figure 2G:
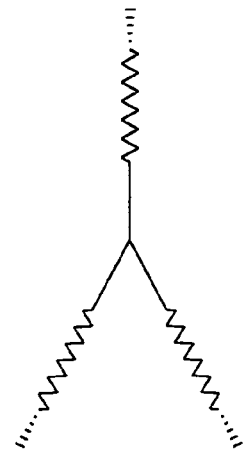
Figure 2H:
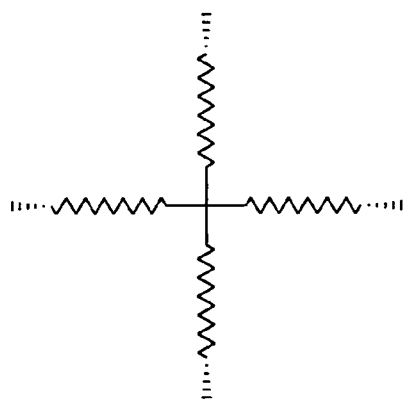
Figure 2J:
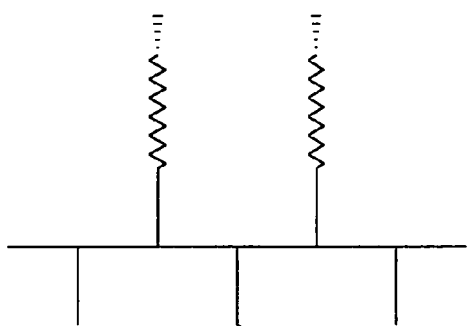
Figure 2I:
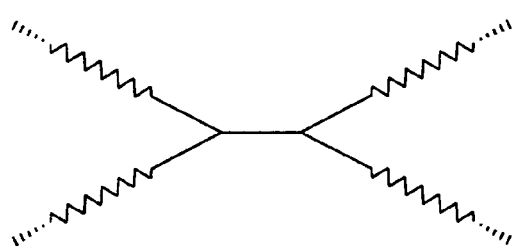

The novel biocompatible crosslinked polymers of this invention are formed from the reaction of precursors having electrophilic and nucleophilic functional groups. The precursors are preferably water soluble, non-toxic and biologically acceptable.

Preferably, at least one of the precursors is a small molecule, and is referred to as a "crosslinker". More preferably, the crosslinker has a solubility of at least 1 g/100 mL in an aqueous solution. Preferably, one of the other precursors is a macromolecule, and is referred to as a "functional polymer".

Functional Groups

Each precursor is multifunctional, meaning that it comprises two or more electrophilic or nucleophilic functional groups, such that a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products. Such reactions are referred to as "crosslinking reactions".

Preferably, each precursor comprises only nucleophilic or only electrophilic functional groups, so long as both nucleophilic and electrophilic precursors are used in the crosslinking reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfosuccinimides, then the functional polymer may have nucleophilic functional groups such as amines. Thus, functional polymers such as proteins, poly(allyl amine); or amine-terminated di- or multifunctional poly(ethylene glycol) ("PEG") can be used.

Water Soluble Cores

The precursors preferably have biologically inert and water soluble cores. When the core is a polymeric region that is water soluble, preferred polymers that may be used include: polyethers, for example polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly (amino acids); dextran and the like. The polyethers and more particularly poly(oxyalkylenes) or poly(ethylene oxide) or polyethylene oxide are especially preferred. When the core is small molecular in nature, any of a variety of hydrophilic functionalities can be used to make the precursor water soluble. For example, functional groups like hydroxyl, amine, sulfonate and carboxylate, which are water soluble, maybe used to make the precursor water soluble. In addition, N-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

Biodegradable Linkages

If it is desired that the biocompatible crosslinked polymer be biodegradable or absorbable, one or more precursors having biodegradable linkages present in between the functional groups may be used. The biodegradable linkage optionally also may serve as the water soluble core of one or more of the precursors. In the alternative, or in addition, the functional groups of the precursors may be chosen such that the product of the reaction between them results in a biodegradable linkage. For each approach, biodegradable linkages may be chosen such that the resulting biodegradable biocompatible crosslinked polymer will degrade or be absorbed in a desired period of time. Preferably, biodegradable linkages are selected that degrade under physiological conditions into non-toxic products.

The biodegradable linkage may be chemically or enzymatically hydrolyzable or absorbable. Illustrative chemically hydrolyzable biodegradable linkages include polymers, copolymers and oligomers of glycolide, dl-lactide, l-lactide, caprolactone, dioxanone, and trimethylene carbonate. Illustrative enzymatically hydrolyzable biodegradable linkages include peptidic linkages cleavable by metalloproteinases and collagenases. Additional illustrative biodegradable linkages include polymers and copolymers of poly(hydroxy acid)s, poly(orthocarbonate)s, poly(anhydride)s, poly(lactone)s, poly(aminoacid)s, poly(carbonate)s, and poly(phosphonate)s.

Visualization Agents

Where convenient, the biocompatible crosslinked polymer or precursor solutions (or both) may contain visualization agents to improve their visibility during surgical procedures. Visualization agents are especially useful when used in MIS procedures, due among other reasons to their improved visibility on a color monitor.

Visualization agents may be selected from among any of the various non-toxic colored substances suitable for use in medical implantable medical devices, such as FD&C dyes 3 and 6, eosin, methylene blue, indocyanine green, or colored dyes normally found in synthetic surgical sutures. The preferred color is green or blue because it has better visibility in presence of blood or on a pink or white tissue background. Red is the least preferred color.

The visualization agent may be present in either a crosslinker or functional polymer solution, preferably in a functional polymer solution. The preferred colored substance may or may not become incorporated into the biocompatible crosslinked polymer. Preferably, however, the visualization agent does not have a functional group capable of reacting with the crosslinker or functional polymer.

The visualization agent may be used in small quantities, preferably less than 1% weight/volume, more preferably less that 0.01% weight/volume and most preferably less than 0.001% weight/volume concentration.

Additional visualization agents may be used, such as fluorescent (e.g., green or yellow fluorescent under visible light) compounds (e.g., fluorescein or eosin), x-ray contrast agents (e.g., iodinated compounds) for visibility under x-ray imaging equipment, ultrasonic contrast agents, or MRI contrast agents (e.g., Gadolinium containing compounds).

Crosslinking Reactions

The crosslinking reactions preferably occur in aqueous solution under physiological conditions. More preferably the crosslinking reactions occur "in situ", meaning they occur at local sites such as on organs or tissues in a living animal or human body. More preferably the crosslinking reactions do not release heat of polymerization. Preferably the crosslinking reaction leading to gelation occurs within 10 minutes, more preferably within 2 minutes, more preferably within one minute, and most preferably within 30 seconds.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Several methods for activating such functional groups are known in the art. Preferred activating groups include carbonyldiimidazole, sulfonyl chloride, aryl halides, sulfosuccinimidyl esters, N-hydroxysuccinimidyl ester, succinimidyl ester, epoxide, aldehyde, maleimides, imidoesters and the like. The N-hydroxysuccinimide esters or N-hydroxysulfosuccinimide groups are the most preferred groups for crosslinking of proteins or amine functionalized polymers such as aminoterminated polyethylene glycol ("APEG").

FIGS. 1 to 5 illustrate various embodiments of preferred crosslinkers and functional polymers.

FIG. 1 illustrates possible configurations of degradable electrophilic crosslinkers or functional polymers. The biodegradable regions are represented by ( ); the functional groups are represented by ( ); and the inert water soluble cores are represented by (—). For crosslinkers, the central core is a water soluble small molecule and for functional polymers the central core is a water soluble polymer of natural or synthetic origin.

When Structure A in FIG. 1 is a functional polymer, it is a linear water soluble and biodegradable functional polymer, end-capped with two functional groups (e.g., N-hydroxysuccinimide ester or NHS, epoxide or similar reactive groups). The water soluble core may be a polyalkylene oxide, preferably polyethylene glycol block copolymer, and it is extended with at least one biodegradable linkage between it and each terminal functional group. The biodegradable linkage may be a single linkage or copolymers or homopolymers of absorbable polymers such as polyhydroxy acids or polylactones.

When Structure B in FIG. 1 is a functional polymer it is a branched or star shaped biodegradable functional polymer which has an inert polymer at the center. Its inert and water soluble core is terminated with oligomeric biodegradable extensions, which in turn are terminated with reactive functional groups.

When Structures C and D in FIG. 1 are functional polymers, they are multifunctional 4 arm biodegradable functional polymers. This polymer again has a water-soluble core at the center, which is a 4 arm, tetrafunctional polyethylene glycol (Structure C) or block copolymer of PEO-PPO-PEO such as Tetronic 908 (Structure D) which is extended with by small oligomeric extensions of biodegradable polymer to maintain water solubility and terminated with reactive functional end-groups such as CDI or NHS.

When Structure E in FIG. 1 is a functional polymer, it is a multifunctional star or graft type biodegradable polymer. This polymer has a water-soluble polymer like polyethylene oxide, polyvinyl alcohol or poly(vinyl pyrrolidinone) at the core which is completely or partially extended with biodegradable polymer. The biodegradable polymer is terminated with reactive end groups.

Structures A-E in FIG. 1 need not have polymeric cores and may be small molecule crosslinkers. In that case, the core may comprise a small molecule like ethoxylated glycerol, inositol, trimethylolpropane etc. to form the resultant crosslinker. In addition, Structures A-E in FIG. 1 need not have polymeric biodegradable extensions, and the biodegradable extensions may consist of small molecules like succinate or glutarate or combinations of 2 or more esters, such as glycolate/2-hydroxybutyrate or glycolate/4-hydroxyproline, etc. A dimer or trimer of 4-hydroxyproline may be used not only to add degradability, but also to add nucleophilic reactive sites via the pendant primary amines which are part of the hydroxyproline moiety.

Other variations of the core, the biodegradable linkage, and the terminal electrophilic group in Structures A-E in FIG. 1 may be constructed, so long as the resulting functional polymer has the properties of low tissue toxicity, water solubility, and reactivity with nucleophilic functional groups.

FIG. 2 illustrates various embodiments of nucleophilic biodegradable water-soluble crosslinkers and functional polymers suitable foe use with electrophilic functional polymers and crosslinkers described herein. The biodegradable regions are represented by ( ); the functional groups are represented by ( ); and the inert water soluble cores are represented by (—). For crosslinkers, the central core is a water soluble small molecule and for functional polymers the central core is a water soluble polymer of natural or synthetic origin.

When Structure F in FIG. 2 is a functional polymer, it is a linear water-soluble biodegradable polymer terminated with reactive functional groups like primary amine. The linear water-soluble core is a polyalkylene oxide, preferably polyethylene glycol block copolymer, which is extended with the biodegradable region which is a copolymer or homopolymer of polyhydroxy acids or polylactones. This biodegradable polymer is terminated with primary amines.

When Structure G in FIG. 2 is a functional polymer, it is a branched or star shaped biodegradable polymer which has an inert polymer at the center. The inert polymer is extended with single or oligomeric biodegradable extensions which are terminated with reactive functional groups.

When Structures H and I in FIG. 2 are functional polymers, they are multifunctional 4 arm biodegradable polymers. These polymers again have water-soluble cores at their center which are either a 4 arm, tetrafunctional polyethylene glycol (Structure H) or a block copolymer of PEO-PPO-PEO such as Tetronic 908 (Structure I), extended with small oligomeric extensions of biodegradable polymers to maintain water solubility, and terminated with functional groups such as amines and thiols.

When Structure J in FIG. 2 is a functional polymer, it is a multifunctional star or graft type biodegradable polymer. This polymer has a water-soluble polymer like polyethylene oxide, polyvinyl alcohol or poly(vinyl pyrrolidinone) at the core which is completely or partially extended with biodegradable polymer. The biodegradable polymer is terminated with reactive end groups.

Structures F-J in FIG. 2 need not have polymeric cores and may be small molecule crosslinkers. In that case, the core may comprise a small molecule like ethoxylated glycerol, inositol, trimethylolpropane etc. to form the resultant crosslinker.

Other variations of the core, the biodegradable linkage, and the terminal nucleophilic group in Structures F-J in FIG. 2 may be constructed, so long as the resulting functional polymer has the properties of low tissue toxicity, water solubility, and reactivity with electrophilic functional groups.

Figure 3K:
FIG. 3 depicts electrophilic water soluble and biodegradable crosslinkers or functional polymers, which can be crosslinked with appropriate nucleophilic precursors, wherein either the biodegradable linkages or the functional groups are selected so as to make the precursor water soluble.
Figure 3L:
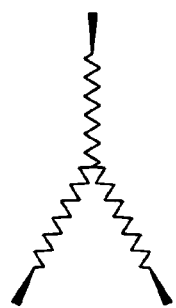

FIG. 3 illustrates configurations of water soluble electrophilic crosslinkers or functional polymers where the core is biodegradable. The biodegradable regions are represented by (ᴡᴡᴡ) and the functional groups are represented by (▶). The biodegradable core is terminated with a reactive functional group that is also water solubilizing, such a N-hydroxysulfosuccinimide ester ("SNHS") or N-hydroxyethoxylated succinimide ester ("ENHS").

Structure K in FIG. 3 depicts a difunctional biodegradable polymer or oligomer terminated with SNHS or ENHS. The oligomers and polymers may be made of a poly(hydroxy acid) such as poly(lactic acid), which is insoluble in water. However, the terminal carboxylic acid group of these oligomers or polymers can be activated with N-hydroxysulfosuccinimide ester ("SNHS") or N-hydroxyethoxylated succinimide ester ("ENHS") groups. An ionic group, like a metal salt (preferably sodium salt) of sulfonic acid, or a nonionic group, like a polyethylene oxide on the succinimide ring, provides water solubility while the NHS ester provides chemical reactivity towards amines. The sulfonate groups (sodium salts) or ethoxylated groups on the succinimide ring solubilize the oligomer or polymer without appreciably inhibiting reactivity towards amine groups.

Structures L-O in FIG. 3 represent multi-branched or graft type structures with terminal SNHS or ENHS group. The cores may comprise various non-toxic polyhydroxy compounds like sugars (xylitol, erythritol), glycerol, trimethylolpropane, which have been reacted with anhydrides such as succinic or glutaric anhydrides. The resultant acid groups were then activated with SNHS or ENHS groups to form water-soluble crosslinkers or functional polymers.

Figure 4R:
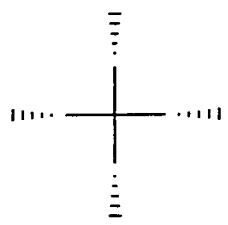
FIG. 4 depicts nucleophilic water soluble crosslinkers or functional polymers, which can be crosslinked with appropriate electrophilic precursors, and which are not biodegradable.
Figure 4S:
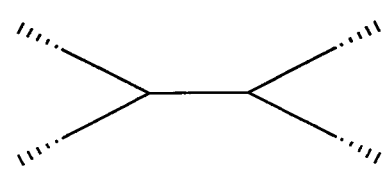
Figure 5U:
FIG. 5 depicts electrophilic water soluble crosslinkers or functional polymers, which can be crosslinked with appropriate nucleophilic precursors, and which are not biodegradable.
Figure 5V:
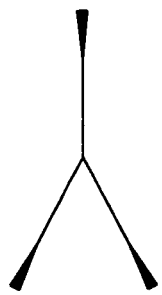
Figure 5W:
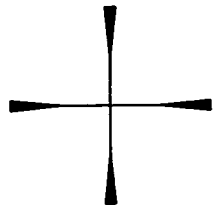
Figure 5Y:
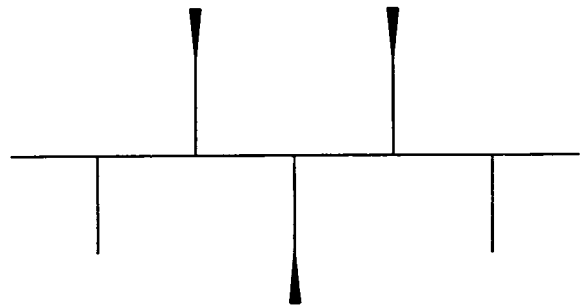
Figure 5X:
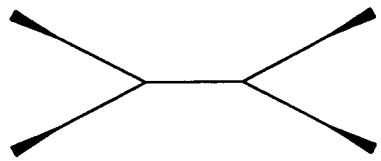

FIG. 4 illustrates various nucleophilic functional polymers or crosslinkers that are not biodegradable. The nucleophilic functional groups are represented by (⁘⁘⁘) and the inert water soluble cores are represented by (—). For crosslinkers, the central core is a water soluble small molecule and for functional polymers the central core is a water soluble polymer of natural or synthetic origin.

When Structure P in FIG. 4 is a functional polymer it may be a water-soluble linear polymer such as polyethylene glycol terminated with reactive end group such as primary amines and thiols. Such polymers are commercially available from Sigma (Milwaukee, Wis.) and Shearwater Polymers (Huntsville, Ala.). Some other preferred difunctional polymers are PPO-PEO-PPO block copolymers such as Pluronic F68 terminated with amine groups. Pluronic or Tetronic polymers are normally available with terminal hydroxyl groups. The hydroxyl groups are converted into amine groups by methods known in the art.

When Structures Q-T in FIG. 4 are functional polymers they may be multifunctional graft or branch type water-soluble copolymers with terminal amine groups.

Structures P-T in FIG. 4 need not have polymeric cores and may be small molecule crosslinkers. In that case, the core may comprise a small molecule like ethoxylated glycerol, inositol, trimethylolpropane, dilysine etc. to form the resultant crosslinker.

Other variations of the core and the terminal nucleophilic group in Structure P-T in FIG. 4 may be employed, so long as the properties of low tissue toxicity, water solubility, and reactivity with electrophilic functional groups are maintained.

FIG. 5 illustrates various electrophilic functional polymers or crosslinkers that are not biodegradable. The electrophilic functional groups are represented by (▶) and the inert water soluble cores are represented by (—). For crosslinkers, the central core is a water soluble small molecule and for functional polymers the central core is a water soluble polymer of natural or synthetic origin.

When Structure U is a functional polymer, it may be a water-soluble polymer such as polyethylene glycol terminated reactive end group such as NHS or epoxide. Such polymers are commercially available from Sigma and Shearwater polymers. Some other preferred polymers are PPO-PEO-PPO block copolymers such as Pluronic F68 terminated with NHS or SNHS group. Pluronic or Tetronic polymers are normally available with terminal hydroxyl groups. The hydroxyl groups are converted into acid group by reacting with succinic anhydride. The terminated acid groups are reacted with N-hydroxysuccinimide in presence of DCC to generate NHS activated Pluronic polymer.

When Structures V-Y are functional polymers they may be multifunctional graft or branch type PEO or PEO block copolymers (Tetronics) activated with terminal reactive groups such as NHS.

Structures U-Y in FIG. 5 need not have polymeric cores and may be small molecule crosslinkers. In that case, the core may comprise a small molecule like ethoxylated glycerol, inositol, trimethylolpropane, dilysine etc. to form the resultant crosslinker.

Other variations of the core and the terminal nucleophilic group in Structures U-Y in FIG. 5 may be employed, so long as the properties of low tissue toxicity, water solubility, and reactivity with electrophilic functional groups are maintained.

Preparation of Structures A-Y in FIGS. 1-5

The polymeric crosslinkers and functional polymers illustrated as Structures A-Y in FIGS. 1 to 5 may be prepared using variety of synthetic methods. Their preferred compositions are described in Table 1.

TABLE 1

Preferred Crosslinkers and Functional Polymers

| Structure | Brief Description | Typical Example |
|---|---|---|
| A | Water soluble, linear difunctional crosslinker or functional polymer with water soluble core, extended with biodegradable regions such as oligomers of hydroxyacids or peptide sequences which are cleavable by enzymes and terminated with protein reactive functional groups. | Polyethylene glycol or ethoxylated propylene glycol chain extended with oligolactate and terminated with N-hydroxysuccinimide esters. |
| B | Water soluble, trifunctional crosslinker or functional polymer with water soluble core, extended with biodegradable regions such as oligomers of hydroxyacids or peptide sequences and terminated with protein reactive functional groups | Ethoxylated glycerol chain extended with oligolactate and terminated with N-hydroxysuccinimide esters |
| C | Water soluble, tetrafunctional crosslinker or functional polymer with water soluble core, extended with biodegradable regions such as oligomers of hydroxyacids or peptide sequences and terminated with protein reactive functional groups | 4 arm polyethylene glycol, erythritol or pentaerythritol chain extended with oligolactate and terminated with N-hydroxysuccinimide esters |
| D | Water soluble, tetrafunctional crosslinker or functional polymer with water soluble core, extended with biodegradable regions such as oligomers of hydroxyacids or peptide sequences and terminated with protein reactive functional groups | Ethoxylated ethylene diamine or polyethylene oxide-polypropylene oxide-polyethylene oxide block copolymer like Tetronic 908 chain extended with oligotrimethylene carbonate and terminated with N-hydroxysuccinimide ester |
| E | Water soluble, branched crosslinker or functional polymer with water soluble core, extended with biodegradable regions such as oligomers of hydroxyacids or peptide sequences and terminated with protein reactive functional groups | Low molecular weight polyvinyl alcohol with 1% to 20% hydroxyl groups extended with oligolactate and terminated with N-hydroxysuccinimide ester |
| F | Water soluble, linear difunctional crosslinker or functional polymer with water soluble core, extended with biodegradable regions such as oligomers of hydroxyacids or peptide sequences and terminated with amines, carboxylic acid or thiols | Polyethylene oxide-polypropylene oxide-polyethylene oxide block copolymer surfactant like Pluronic F68 chain extended with oligolactate and terminated with amino acids such as lysine or peptide sequences that may contain two amine groups |
| G | Water soluble, trifunctional crosslinker or functional polymer with water soluble core, extended with biodegradable regions such as oligomers of hydroxyacids or peptide sequences and terminated with amines, carboxylic acid or thiols | Ethoxylated glycerol chain extended with oligolactate and terminated with aminoacid such as lysine |
| H | Water soluble, tetrafunctional crosslinker or functional polymer with water soluble core, extended with biodegradable regions such as oligomers of hydroxyacids or peptide sequences and terminated with amines, carboxylic acid or thiols | 4 arm polyethylene glycol or tetra erythritol chain extended with oligolactate and terminated with aminoacid such as lysine |
| I | Water soluble, tetrafunctional crosslinker or functional polymer with water soluble core, extended with biodegradable regions such as oligomers of hydroxyacids or peptide sequences and terminated with amines, carboxylic acid or thiols | Ethoxylated ethylene diamine or polyethylene oxide-polypropylene oxide-polyethylene oxide block copolymer like Tetronic 908 chain extended with oligotrimethylene carbonate and terminated with aminoacid such as lysine |
| J | Water soluble, multifunctional or graft type crosslinker or functional polymer with water soluble core, extended with biodegradable regions such as oligomers of hydroxyacids or peptide sequences and terminated with amines, carboxylic acid or thiols | Low molecular weight polyvinyl alcohol with 1-20% hydroxyl groups extended with oligolactate and terminated with aminoacid such as lysine |
| K | Water soluble, linear difunctional crosslinker or functional polymer such as oligomers of hydroxyacids or peptide sequences which are terminated with protein reactive functional groups | Difunctional oligolactic acid with terminal carboxyl groups which are activated with n-hydroxysulfosuccinimide ester or ethoxylated n-hydroxysuccinimide ester. |
| L | Water soluble branched | Trifunctional |

TABLE 1-continued

Preferred Crosslinkers and Functional Polymers

| Structure | Brief Description | Typical Example |
|---|---|---|
| | trifunctional crosslinker or functional polymer such as oligomers of hydroxyacids or peptide sequences which are terminated with protein reactive functional groups | oligocaprolactone with terminal carboxyl groups which are activated with n-hydroxysulfosuccinimide ester or ethoxylated n-hydroxysuccinimide ester. |
| M | Water soluble, branched tetrafunctional crosslinker or functional polymer such as oligomers of hydroxyacids or peptide sequences which are terminated with protein reactive functional groups | Tetrafunctional oligocaprolactone with terminal carboxyl groups which are activated with n-hydroxysulfosuccinimide ester or ethoxylated n-hydroxysuccinimide ester. |
| N | Water soluble, branched tetrafunctional crosslinker or functional polymer such as oligomers of hydroxyacids or peptide sequences which are terminated with protein reactive functional groups | Tetrafunctional oligocaprolactone with terminal carboxyl groups which are activated with n-hydroxysulfosuccinimide ester or ethoxylated n-hydroxysuccinimide ester. |
| O | Water soluble, branched multifunctional crosslinker or functional polymer such as oligomers of hydroxyacids or peptide sequences which are terminated with protein reactive functional groups | Multifunctional oligolactic acid with terminal carboxyl groups which are activated with n-hydroxysulfosuccinimide ester or ethoxylated n-hydroxysuccinimide ester. |
| P | Water soluble, linear difunctional crosslinker or functional polymer terminated with amines, carboxylic acid or thiols functional groups | Polyethylene glycol with terminal amines groups |
| Q | Water soluble, branched trifunctional crosslinker or functional polymer terminated with amines, carboxylic acid or thiols as functional group | Ethoxylated glycerol with terminal amines groups |
| R | Water soluble, branched tetrafunctional crosslinker or functional polymer terminated with amines, carboxylic acid or thiols functional groups | 4 arm polyethylene glycol modified to produce terminal amine groups |
| S | Water soluble, branched tetrafunctional crosslinker or functional polymer terminated with amines, carboxylic acid or thiols functional groups | Ethoxylated ethylene diamine or polyethylene oxide-polypropylene oxide-polyethylene oxide block copolymer like Tetronic 908 modified to generate terminal amine groups |
| T | Water soluble, branched or graft crosslinker or functional polymer with terminal amines, carboxylic acid or thiols functional groups | Polylysine, albumin, polyallyl amine |
| U | Water soluble, linear difunctional crosslinker or functional polymer terminated with protein reactive functional groups | Polyethylene glycol with n-hydroxysuccinimide as end groups |
| V | Water soluble branched trifunctional crosslinker or functional polymer terminated with protein reactive functional groups | Ethoxylated glycerol terminated with n-hydroxysuccinimide |
| W | Water soluble branched tetrafunctional crosslinker or functional polymer terminated with protein reactive functional groups | 4 arm polyethylene glycol terminated with n-hydroxysuccinimide esters |
| X | Water soluble branched tetrafunctional crosslinker or functional polymer terminated with protein reactive functional groups | Ethoxylated ethylene diamine or polyethylene oxide-polypropylene oxide-polyethylene oxide block copolymer like Tetronic 908 with n-hydroxysuccinimide ester as end group |
| Y | Water soluble, branched or graft polymer crosslinker or functional polymer with protein reactive functional groups | Poly (vinyl pyrrolidinone)-co-poly(n-hydroxysuccinimide acrylate) copolymer (9:1), molecular weight <40000 Da |

First, the biodegradable links of Structures A-J in FIGS. 1 and 2 may be composed of specific di or multifunctional synthetic amino acid sequences which are recognized and cleaved by enzymes such as collagenase, and may be synthesized using methods known to those skilled in the peptide synthesis art. For example, Structures A-E in FIG. 1 may be obtained by first using carboxyl, amine or hydroxy terminated polyethylene glycol as a starting material for building a suitable peptide sequence. The terminal end of the peptide sequence is converted into a carboxylic acid by reacting succinic anhydride with an appropriate amino acid. The acid group generated is converted to an NHS ester by reaction with N-hydroxysuccinimide.

The functional polymers described in FIG. 2 may be prepared using a variety of synthetic methods. In a preferred embodiment, the polymer shown as Structure F may be obtained by ring opening polymerization of cyclic lactones or carbonates initiated by a dihydroxy compound such as Pluronic F 68 in the presence of a suitable catalyst such as stannous 2-ethylhexanoate. The molar equivalent ratio of caprolactone to Pluronic is kept below 10 to obtain a low molecular weight chain extension product so as to maintain water solubility. The terminal hydroxyl groups of the resultant copolymer are converted into amine or thiol by methods known in the art.

In a preferred method, the hydroxyl groups of a Pluronic-caprolactone copolymer are activated using tresyl chloride. The activated groups are then reacted with lysine to produce lysine terminated Pluronic-caprolactone copolymer. Alternatively, an amine-blocked lysine derivative is reacted with the hydroxyl groups of a Pluronic-caprolactone copolymer and then the amine groups are regenerated using a suitable deblocking reaction.

Structures G, H, I and J in FIG. 2 may represent multifunctional branched or graft type copolymers having water-soluble core extended with oligohydroxy acid polymer and terminated with amine or thiol groups.

Figure 6:
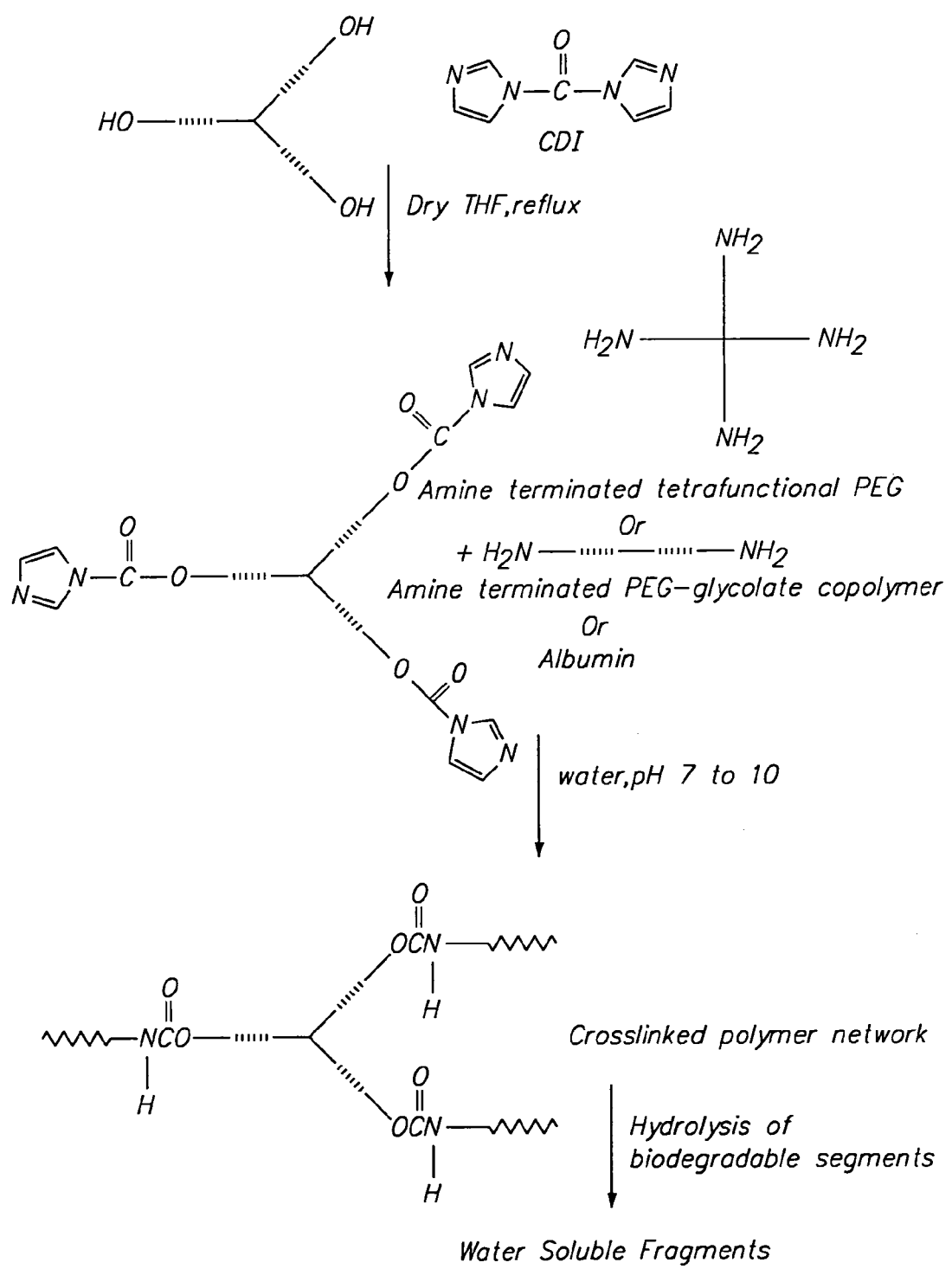
FIG. 6 depicts the preparation of an electrophilic water soluble crosslinker or functional polymer using carbodiimide ("CDI") activation chemistry, its crosslinking reaction with a nucleophilic water soluble functional polymer to form a biocompatible crosslinked polymer product, and the hydrolysis of that biocompatible crosslinked polymer to yield water soluble fragments.
Figure 7:
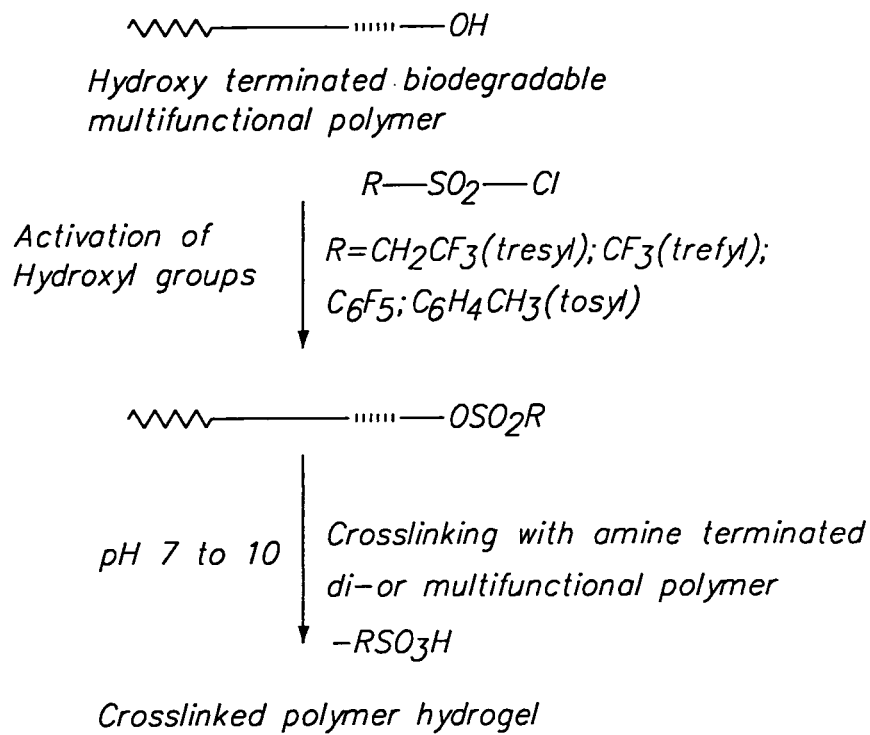
FIG. 7 depicts the use of sulfonyl chloride activation chemistry to prepare an electrophilic functional polymer.

For example, in a preferred embodiment, the functional polymer illustrated as Structure G in FIG. 2 is obtained by ring opening polymerization of cyclic lactones or carbonates initiated by a tetrahydroxy compound such as 4 arm, tetrahydroxy polyethylene glycol (molecular weight 10,000 Da), in the presence of a suitable catalyst such as stannous octoate. The molar equivalent ratio of cyclic lactone or carbonate to PEG is kept below 10 to obtain a low molecular weight extension, and to maintain water solubility (polymers of cyclic lactones generally are not as water soluble as PEG). Alternatively, hydroxyacid as a biodegradable link may be attached to the PEG chain using blocking/deblocking chemistry known in the peptide synthesis art. The terminal hydroxy groups of the resultant copolymer are activated using a variety of reactive groups known in the art. The CDI activation chemistry and sulfonyl chloride activation chemistry is shown in FIGS. 6 and 7, respectively.

Figure 8:
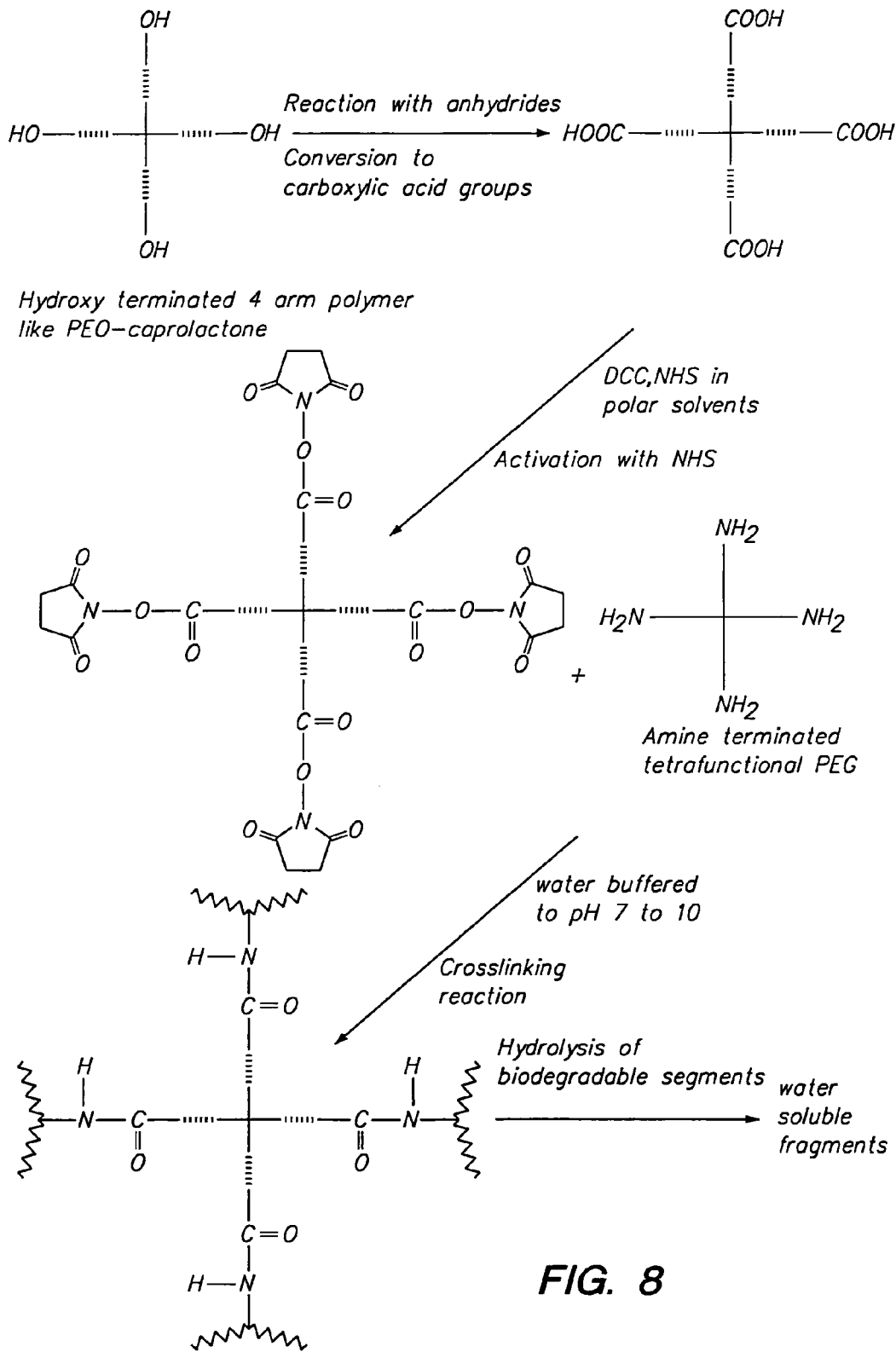
FIG. 8 depicts the preparation of an electrophilic water soluble crosslinker or functional polymer using N-hydroxysuccinimide ("NHS") activation chemistry, its crosslinking reaction with a nucleophilic water soluble functional polymer to form a biocompatible crosslinked polymer product, and the hydrolysis of that biocompatible crosslinked polymer to yield water soluble fragments.
Figure 9:
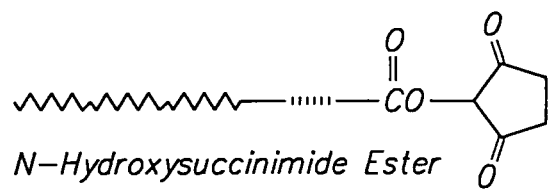
FIG. 9 depicts preferred NHS esters for use in the invention.
Figure 9:
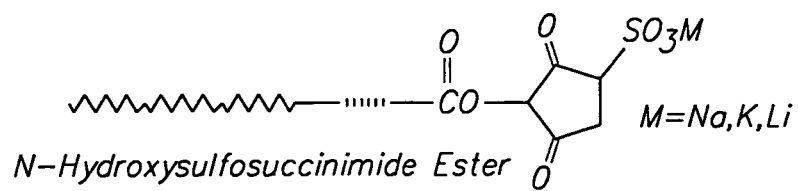
Figure 9:
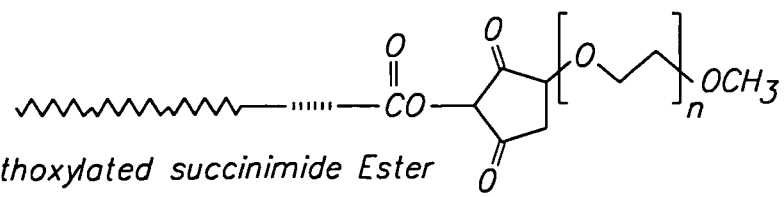
Figure 10:
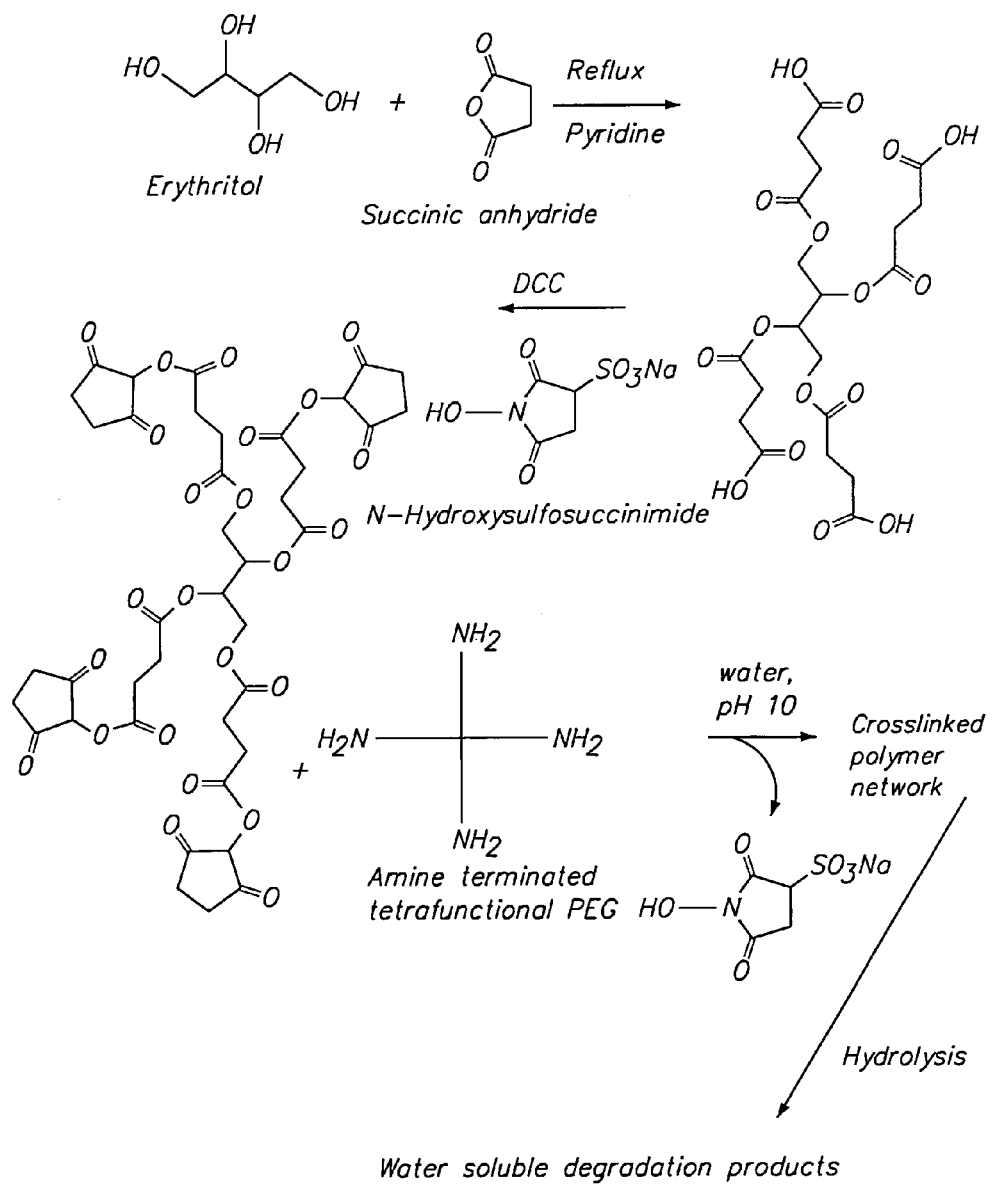
FIG. 10 shows the N-hydroxysulfosuccinimide ("SNHS") activation of a tetrafunctional sugar-based water soluble synthetic crosslinker and its crosslinking reaction with 4-arm amine terminated polyethylene glycol to form a biocompatible crosslinked polymer product, and the hydrolysis of that biocompatible crosslinked polymer to yield water soluble fragments.

The most preferred reactive groups are N-hydroxysuccinimide esters, synthesized by any of several methods. In a preferred method, hydroxyl groups are converted to carboxylic groups by reacting them with anhydrides such as succinic anhydride in the presence of tertiary amines such as pyridine or triethylamine or dimethylaminopyridine ("DMAP"). Other anhydrides such as glutaric anhydride, phthalic anhydride, maleic anhydride and the like may also be used. The resultant terminal carboxyl groups are reacted with N-hydroxysuccinimide in the presence of dicyclohexylcarbodiimide ("DCC") to produce N-hydroxysuccinimide ester (referred as NHS activation). The NHS activation and crosslinking reaction scheme is shown in FIG. 8. The most preferred N-hydroxysuccinimide esters are shown in FIG. 9.

In a preferred embodiment, the polymer shown as structure H is obtained by ring opening polymerization of glycolide or trimethylene carbonate initiated by a tetrahydroxy compound such as tetrafunctional polyethylene glycol (molecular weight 2000 Da) in the presence of a catalyst such as stannous 2-ethylhexoate. The molar equivalent ratio of glycolide to PEG is kept from 2 to 10 to obtain a low molecular weight extension. The terminal hydroxy groups of the resultant copolymer are converted into amine groups by reaction with lysine as mentioned previously. Similar embodiments can be obtained using analogous chain extension synthetic strategies to obtain structures F, G, I and J by starting with the appropriate corresponding polyol.

Structures K, L, M, N, and O in FIG. 3 are made using a variety of synthetic methods. In a preferred embodiment, the polymer shown as Structure L in FIG. 3 is obtained by ring opening polymerization of cyclic lactones by a trihydroxy compound such as glycerol in the presence of a catalyst such as stannous 2-ethylhexanoate. The molar equivalent ratio of cyclic lactone to glycerol is kept below 2, so that only low molecular weight oligomers are obtained. The low molecular weight oligomer ester is insoluble in water. The terminal hydroxy groups of the resultant copolymer are activated using N-hydroxysulfosuccinimide groups. This is achieved by converting hydroxy groups to carboxylic groups by reacting with anhydrides such as succinic anhydride in presence of tertiary amines. The resultant terminal carboxyl groups are reacted with N-hydroxysulfosuccinimide or N-hydroxyethoxylated succinimide in the presence of dicyclohexylcarbodiimide ("DCC") to produce a sulfonated or ethoxylated NHS ester. The sulfonate or PEO chain on the succinimide ring gives water solubility to the oligoester.

The foregoing method generally is applied to solubilize only low molecular weight multi-branched oligoesters, with molecular weights below 1000. In another variation of this method, various non-toxic polyhydroxy compounds, preferably sugars, such as erythritol, xylitol are reacted with succinic anhydride in the presence of a tertiary amine. The terminal carboxyl group of succinated erythritol is esterified with N-hydroxysulfosuccinimide (FIG. 9). Similar embodiments may be obtained using analogous synthetic strategies to obtain structures K, and M-O by starting with the appropriate starting materials.

Structures P-R may be synthesized by reacting the appropriate starting material, such as a linear (P) or 2- or 3-arm branched PEG (Q, R) with hydroxy end groups, with lysine as mentioned previously, such that the arms of the PEG oligomers are capped with amine end groups. Structure S may be synthesized, using a multistep reaction, from PEG, glycerol and a diisocyanate. In the first step a PEG diol is reacted with excess diisocyanate, such as 4,4'diphenyl methane diisocyanate ("MDI"), methylene-bis(4-cyclohexylisocyanate) ("HMDI") or hexamethylenediisocyanate ("HDI"). After purification the resultant PEG diisocyanate is added dropwise to excess glycerol or trimethylol propane or other triol and reacted to completion. The purified product, now having diol end groups, is again reacted with excess diisocyanate and purified, yielding a PEG-tetra-isocyanate. This tetrafunctional PEG subsequently may be reacted with excess PEG diols, yielding a 4 arm PEG synthesized from a PEG diol oligomer. In the final step lysine end groups are incorporated, as discussed previously.

Structure T may be synthesized as follows. First synthesize a random copolymer of PEG-monoacrylate and some other acrylate or combination of acrylates, such that the final polyacrylate is water soluble. Other acrylates include, but are not limited to, 2-hydroxyethylacrylate, acrylic acid, and acrylamide. Conditions may be varied to control the molecular weight as desired. In the final step, the acrylate is reacted with lysine as discussed previously, using an appropriate quantity to achieve the desired degree of amination.

One method of synthesizing Structures U-Y is to use dicyclohexylcarbodiimide coupling to a carboxylate end group. For Structures U-W, one can react the appropriate PEG-diol, -triol or -tetra-hydroxy starting material with excess succinic anhydride or glutaric anhydride such that all end groups are effectively carboxylated. Structures X and Y may be made in a manner similar to that used for Structures S and T, except that in the last step, instead of end capping with lysine, end capping with succinic anhydride or glutaric anhydride is performed.

Preparation of Biocompatible Polymers

Several biocompatible crosslinked polymers may be produced using the crosslinkers and functional polymers described in FIGS. 1 to 5. Preferred combinations of such polymers suitable for producing such biocompatible crosslinked polymers are described in Table 1 and Table 2. In Table 2, the crosslinker functional groups are N-hydroxy succinimide esters and the functional polymer functional groups are primary amines.

TABLE 2

Biocompatible Polymers Synthesized from Crosslinkers and Functional Polymers Of Table 1

| Crosslinker Structure | Functional Polymer Structure | Concentration | Medium |
|---|---|---|---|
| B or C | H and R | Molar Equivalent; >20% W/V | Borate or triethanol amine buffer, pH 7-9 |
| A, B or C | H, P, Q, R and S | Molar Equivalent; >20% W/V | Borate or triethanol amine buffer, pH 7-9 |
| Y | T, H, P and Q | Molar Equivalent; >10% W/V | Borate or triethanol amine buffer, pH 7-9 |
| W, V | H and J | Molar Equivalent; >10% W/V | Bicarbonate buffer, pH 9 |
| X | I, J and H | Molar Equivalent; >20% W/V | Borate or triethanol amine buffer, pH 7-9 |

The reaction conditions for crosslinking will depend on the nature of the functional groups. Preferred reactions are conducted in buffered aqueous solutions at pH 5 to 12. The preferred buffers are sodium borate buffer (pH 10) and triethanol amine buffer (pH 7). In some embodiments, organic solvents such as ethanol or isopropanol may be added to improve the reaction speed or to adjust the viscosity of a given formulation.

The synthetic crosslinked gels described above degrade due to hydrolysis of the biodegradable region. The degradation of gels containing synthetic peptide sequences will depend on the specific enzyme and its concentration. In some cases, a specific enzyme may be added during the crosslinking reaction to accelerate the degradation process.

When the crosslinker and functional polymers are synthetic (for example, when they are based on polyalkylene oxide), then it is desirable and in some cases essential to use molar equivalent quantities of the reactants. In some cases, molar excess crosslinker may be added to compensate for side reactions such as reactions due to hydrolysis of the functional group.

When choosing the crosslinker and crosslinkable polymer, at least one of polymers must have more than 2 functional groups per molecule and at least one degradable region, if it is desired that the resultant biocompatible crosslinked polymer be biodegradable. For example, the difunctional crosslinker shown as Structure A in FIG. 1 cannot form a crosslinked network with the difunctional polymers shown as Structure F in FIG. 2 or Structure P in FIG. 4. Generally, it is preferred that each biocompatible crosslinked polymer precursor have more than 2 and more preferably 4 functional groups.

Preferred electrophilic groups are NHS, SNHS and ENHS (FIG. 9). Preferred nucleophilic groups are primary amines. The advantage of the NHS-amine reaction is that the reaction kinetics lead to quick gelation usually within 10 minutes, more usually within 1 minute and most usually within 10 seconds. This fast gelation is preferred for in situ reactions on live tissue.

The NHS-amine crosslinking reaction leads to formation of N-hydroxysuccinimide as a side product. The sulfonated or ethoxylated forms of N-hydroxysuccinimide are preferred due to their increased solubility in water and hence their rapid clearance from the body. The sulfonic acid salt on the succinimide ring does not alter the reactivity of NHS group with the primary amines.

The NHS-amine crosslinking reaction may be carried out in aqueous solutions and in the presence of buffers. The preferred buffers are phosphate buffer (pH 5.0-7.5), triethanolamine buffer (pH 7.5-9.0) and borate buffer (pH 9.0-12) and sodium bicarbonate buffer (pH 9.0-10.0).

Aqueous solutions of NHS based crosslinkers and functional polymers preferably are made just before the crosslinking reaction due to reaction of NHS groups with water. Longer "pot life" may be obtained by keeping these solutions at lower pH (pH 4-5).

The crosslinking density of the resultant biocompatible crosslinked polymer is controlled by the overall molecular weight of the crosslinker and functional polymer and the number of functional groups available per molecule. A lower molecular weight between crosslinks such as 600 Da will give much higher crosslinking density as compared to a higher molecular weight such as 10,000 Da. Higher molecular weight functional polymers are preferred, preferably more than 3000 Da, so as to obtain elastic gels.

The crosslinking density also may be controlled by the overall percent solids of the crosslinker and functional polymer solutions. Increasing the percent solids increases the probability that an electrophilic group will combine with a nucleophilic group prior to inactivation by hydrolysis. Yet another method to control crosslink density is by adjusting the stoichiometry of nucleophilic groups to electrophilic groups. A one to one ratio leads to the highest crosslink density.

Preparation of Biodegradable Polymers

The biodegradable crosslinkers described in FIGS. 1 and 3 may be reacted with proteins, such as albumin, other serum proteins, or serum concentrates to generate crosslinked polymeric networks. Briefly, aqueous solutions of the crosslinkers described in FIG. 1 and FIG. 3 (at a concentration of 50 to 300 mg/ml) are mixed with concentrated solutions of albumin (600 mg/ml) to produce a crosslinked hydrogel. This reaction can be accelerated if a buffering agent, e.g., borate buffer or triethanol amine, is added during the crosslinking step.

The resultant crosslinked hydrogel is a semisynthetic hydrogel whose degradation depends on the degradable segment in the crosslinker as well as degradation of albumin by enzymes. In the absence of any degradable enzymes, the crosslinked polymer will degrade solely by the hydrolysis of the biodegradable segment. If polyglycolate is used as the biodegradable segment, the crosslinked polymer will degrade in 1-30 days depending on the crosslinking density of the network. Similarly, a polycaprolactone based crosslinked network will degrade in 1-8 months. The degradation time generally varies according to the type of degradable segment used, in the following order: polyglycolate<polylactate<polytrimethylene carbonate<polycaprolactone. Thus, it is possible to construct a hydrogel with a desired degradation profile, from a few days to months, using a proper degradable segment.

The hydrophobicity generated by biodegradable blocks such as oligohydroxy acid blocks or the hydrophobicity of PPO blocks in Pluronic or Tetronic polymers are helpful in dissolving small organic drug molecules. Other properties which will be affected by incorporation of biodegradable or hydrophobic blocks are: water absorption, mechanical properties and thermosensitivity.

Methods of Using Biocompatible Polymers

The biocompatible crosslinked polymers and their precursors described above may be used in a variety of applications, such as components of tissue adhesives, tissue sealants, drug delivery vehicles, wound covering agents, barriers in preventing postoperative adhesions, and others. These and other suitable applications are reviewed in Schlag and Redl, "Fibrin Sealant" in *Operative Surgery*, volumes 1-7 (1986), which is incorporated herein by reference.

In Situ Formation

In many applications, the biocompatible crosslinked polymers of this invention typically will be formed "in situ" at a surgical site in the body. The various methodologies and devices for performing "in situ" gelation, developed for other adhesive or sealant systems such fibrin glue or sealant applications, may be used with the biocompatible crosslinked polymers of this invention. Thus, in one embodiment, an aqueous solution of a freshly prepared crosslinker (e.g., SNHS-terminated oligolactide synthesized from a glycerol core in phosphate buffered saline ("PBS") at pH 5 to 7.2) and a functional polymer (e.g., albumin or amine terminated tetrafunctional polyethylene glycol at pH 10 in sodium borate) are applied and mixed on the tissue using a double barrel syringe (one syringe for each solution). The two solutions may be applied simultaneously or sequentially. In some embodiments, it is preferred to apply the precursor solutions sequentially so as to "prime" the tissue, resulting in improved adherence of the biocompatible crosslinked polymer to the tissue. Where the tissue is primed, the crosslinker precursor is preferably applied to the tissue first, followed by the functional polymer solution.

One may use specialized devices to apply the precursor solutions, such as those described in U.S. Pat. Nos. 4,874,368; 4,631,055; 4,735,616; 4,359,049; 4,978,336; 5,116,315; 4,902,281; 4,932,942; Published Patent Cooperation Treaty Patent Application No. WO 91/09641; and R. A. Tange, "Fibrin Sealant" in *Operative Medicine: Otolaryngology*, volume 1 (1986), the disclosures of which are herein incorporated by reference.

Drug Delivery

The subject crosslinkers, functional polymer and their reaction products, the crosslinked materials advantageously may be used for localized drug therapy. Biologically active agents or drug compounds that may be added and delivered from the crosslinked polymer or gel include: proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides.

To prepare such crosslinked composition, the bioactive compounds described above are mixed with the crosslinkable polymer prior to making the aqueous solution or during the aseptic manufacturing of the functional polymer. This mixture then is mixed with the crosslinker to produce a crosslinked material in which the biologically active substance is entrapped. Functional polymers made from inert polymers like Pluronic, Tetronics or Tween™ surfactants are preferred in releasing small molecule hydrophobic drugs.

In a preferred embodiment, the active agent or agents are present in a separate phase when crosslinker and crosslinkable polymers are reacted to produce a crosslinked polymer network or gel. This phase separation prevents participation of bioactive substance in the chemical crosslinking reaction such as reaction between NHS ester and amine group. The separate phase also helps to modulate the release kinetics of active agent from the crosslinked material or gel, where 'separate phase' could be oil (oil-in water emulsion), biodegradable vehicle; and the like. Biodegradable vehicles in which the active agent may be present include: encapsulation vehicles, such as microparticles, microspheres, microbeads, micropellets, and the like, where the active agent is encapsulated in a bioerodable or biodegradable polymers such as polymers and copolymers of: poly(anhydride), poly(hydroxy acid)s, poly(lactone)s, poly(trimethylene carbonate), poly(glycolic acid), poly(lactic acid), poly(glycolic acid)-co-poly (glycolic acid), poly(orthocarbonate), poly(caprolactone), crosslinked biodegradable hydrogel networks like fibrin glue or fibrin sealant, caging and entrapping molecules, like cyclodextrin, molecular sieves and the like. Microspheres made from polymers and copolymers of poly(lactone)s and poly (hydroxy acid) are particularly preferred as biodegradable encapsulation vehicles.

In using crosslinked materials which are described herein as drug delivery vehicles, the active agent or encapsulated active agent may be present in solution or suspended form in crosslinker component or functional polymer solution component. The nucleophilic component, whether it be in the crosslinker or the functional polymer is the preferred vehicle due to absence of reactive groups. The functional polymer along with bioactive agent, with or without encapsulating vehicle, is administered to the host along with equivalent amount of crosslinker and aqueous buffers. The chemical reaction between crosslinker and the functional polymer solution readily takes place to form a crosslinked gel and acts as a depot for release of the active agent to the host. Such methods of drug delivery find use in both systemic and local administration of an active agent.

In using the crosslinked composition for drug delivery as mentioned above, the amount of crosslinkable polymer, crosslinker and the dosage agent introduced in the host will necessarily depend upon the particular drug and the condition to be treated. Administration may be by any convenient means such as syringe, canula, trocar, catheter and the like.

Controlled rates of drug delivery also may be obtained with the system of the present invention by degradable, covalent attachment of the bioactive molecules to the crosslinked hydrogel network. The nature of the covalent attachment can be controlled to enable control of the release rate from hours to weeks or longer. By using a composite made from linkages with a range of hydrolysis times, a controlled release profile may be extended for longer durations.

Composite Biomaterials

The biocompatible crosslinked polymers of this invention optionally may be reinforced with flexible or rigid fibers, fiber mesh, fiber cloth and the like. The insertion of fibers improves mechanical properties like flexibility, strength, and tear resistance. In implantable medical applications, biodegradable fibers, cloth, or sheets made from oxidized cellulose or poly (hydroxy acid)s polymers like polylactic acid or polyglycolic acid, are preferred. Such reinforced structures may be produced using any convenient protocol known in the art.

In a preferred method, aqueous solutions of functional polymers and crosslinkers are mixed in appropriate buffers and proportions are added to a fiber cloth or net such as Interceed (Ethicon Inc., New Brunswick, N.J.). The liquid mixture flows into the interstices of the cloth and becomes crosslinked to produce a composite hydrogel. Care is taken to ensure that the fibers or fiber mesh are buried completely inside the crosslinked hydrogel material. The composite structure can be washed to remove side products such as N-hydroxysuccinimide. The fibers used are preferably hydrophilic in nature to ensure complete wetting of the fibers by the aqueous gelling composition.

EXAMPLES

The following non-limiting examples are intended to illustrate the synthesis of new biocompatible crosslinked polymers and their precursors, and their use in making several medical products. Those skilled in the art will appreciate that modifications can be made to these examples, drawings, illustrations and claims that are intended to fall within the scope the present invention.

Materials and Equipment

Polyethylene glycol was purchased form various sources such as Shearwater Polymers, Union Carbide, Fluka and Polysciences. Multifunctional hydroxyl and amine terminated polyethylene glycol were purchased from Shearwater Polymers, Dow Chemicals and Texaco. Pluronic® and Tetronic® series polyols were purchased from BASF Corporation. DL-lactide, glycolide, caprolactone and trimethylene carbonate was obtained from commercial sources like Purac, DuPont, Polysciences, Aldrich, Fluka, Medisorb, Wako and Boehringer Ingelheim. N-hydroxysulfosuccinimide was purchased from Pierce. All other reagents, solvents were of reagent grade and were purchased from commercial sources such as Polysciences, Fluka, Aldrich and Sigma. Most of the reagents and solvents were purified and dried using standard laboratory procedures such as described in D. D. Perrin et al., *Purification of Laboratory Chemicals* (Pergamon Press 1980).

General Analysis

The polymers synthesized according to these examples were chemically analyzed using structure-determining methods such as nuclear (proton and carbon-13) magnetic resonance spectroscopy, infrared spectroscopy. Molecular weights were determined using high pressure liquid chromatography and gel permeation chromatography. Thermal characterization of the polymers, including melting point and glass transition temperatures, were performed using differential scanning calorimetric analysis. Aqueous solution properties such as micelle and gel formation was determined using fluorescence spectroscopy, UV-visible spectroscopy and laser light scattering instruments.

In vitro degradation of the polymers was followed gravimetrically at 37° C., in an aqueous buffered medium such as phosphate buffered saline (at pH 7.2). In vivo biocompatibility and degradation life times was assessed by injecting or forming a gelling formulation directly into the peritoneal cavity of a rat or rabbit and observing its degradation over a period of 2 days to 12 months.

Alternatively, the degradation was also assessed by prefabricating a sterile implant, made by a process like solution casting, then surgically implanting the implant within an animal body. The degradation of the implant over time was monitored gravimetrically or by chemical analysis. The biocompatibility of the implant was assessed by standard histological techniques.

Example 1

Synthesis of a Water-Soluble Difunctional, Biodegradable Functional Polymer Based on Polyalkylene Oxide Block Copolymer First, Polyethylene glycol-co-polycaprolactone polyol ("F68C2") was synthesized as follows:

30 g of Pluronic F68 was dried under vacuum at 110° C. for 6 h and then mixed with 1.710 g of caprolactone and 30 mg of stannous 2-ethylhexanoate in a glass sealing tube. The glass tube then was sealed under nitrogen atmosphere and heated to 170° C. and maintained at this temperature for 16 h. The Pluronic F68-caprolactone polymer was cooled and recovered by breaking the glass sealing tube, and then further purified by several precipitations from a toluene-hexane solvent-nonsolvent system.

The polymer then was dried in vacuum at 40° C. and used immediately in the activation reaction described below:

Reaction with succinic anhydride ("F68C2S"):

30 g of Pluronic F68-caprolactone copolymer was dissolved in 200 ml dry N,N-dimethyl formamide ("DMF") and 0.845 g of succinic anhydride was added to the reaction mixture. The mixture was heated to 100° C. under a nitrogen atmosphere for 16 h. The solution then was cooled and added to 4000 ml hexane to precipitate the carboxyl terminated polymer. It was further purified by repeated (3 times) precipitation from a toluene-hexane solvent-nonsolvent system. The polymer was dried under vacuum at 40° C.

This polymer was immediately used in activation reaction described below:

Activation of carboxyl groups with N-hydroxysuccinimide ("F68C2SSNHS"):

30 g of Pluronic F68-caprolactone succinate copolymer was dissolved in 200 ml dry DMF. The solution was cooled to 4° C. and 1.504 g of 1,3-dicyclohexyl carbodiimide ("DCC") and 1.583 g of N-hydroxysulfosuccinimide ("SNHS") were added to the reaction mixture. The mixture was stirred at 4° C. for 6 h and then stirred overnight at room temperature under nitrogen atmosphere. Dicyclohexylurea was removed by filtration and the F68C2S-SNHS derivative was isolated by removing the DMF under vacuum and repeated precipitation using a toluene-hexane solvent-nonsolvent system. The product was stored under nitrogen atmosphere at −20° C.

Example 2

Amine Terminated Synthetic Biodegradable Crosslinkable Polymer

Reaction of F68TMC2SSNHS with Lysine:

3.55 g of lysine was dissolved in 200 ml 0.1 M borate buffer (pH 8.5). The mixture was cooled to 0° C. in ice bath and 10 g of F68C2SSNHS were added to the mixture. The mixture was stirred for 6 h at room temperature and lyophilized. The lyophilized powder was dissolved in 30 ml toluene and filtered. The filtrate was added to 4000 ml cold diethyl ether. The precipitated amine terminated polymer was recovered by filtration and dried under vacuum. The polymer was stored under argon at −20° C.

Example 3

Synthesis of Carboxyl Terminated Oligolactic Acid Polymer Activated with N-Hydroxysulfosuccinimide Synthesis of Difunctional Oligolactate with terminal carboxyl acid end-groups activated with N-hydroxysulfosuccinimide groups.

Part 1: Synthesis of oligomeric poly(lactic acid) with terminal carboxyl acid groups ("PLA-S"):

In a 250 ml 3 neck flask equipped with mechanical stirrer, nitrogen inlet and distillation condenser, 2 grams of succinic acid and 34.1 ml 1N HCl and 3.83 g L-lactic acid, sodium salt were charged. The flask was then immersed in a silicone oil bath maintained at 150° C. Most of the water from the reaction mixture was removed over period of 5 hours by distillation. The remaining water was removed by heating the reaction mixture under vacuum at 180° C. for 15 h. The reaction mixture was cooled and lyophilized at 0° C. to remove traces of water. The product was isolated by dissolving in toluene and precipitating in hexane. The precipitated polymer was isolated by filtration and dried in vacuum for 48 h at 60° C.

Part 2: Activation of terminal groups with N-hydroxysulfosuccinimide group:

A 3 necked flask equipped with magnetic stirrer and nitrogen inlet was charged with 2 g of PLA-S copolymer and 20 ml DMF. The solution was cooled 4° C. and 3.657 g of N-hydroxysulfosuccinimide and 3.657 g of 1,3-dicyclohexyl carbodiimide were added to the reaction mixture. The mixture was stirred at 4° C. for 6 h and overnight at room temperature under nitrogen atmosphere. Dicyclohexylurea was removed by filtration and SNHS derivative was by isolated by removing the DMF under vacuum and repeated precipitation using toluene-hexane solvent-nonsolvent system. The product was stored under nitrogen atmosphere at 4° C.

Example 4

Preparation of Polyethylene Glycol Based Tetrafunctional Crosslinker

Part 1: Synthesis of tetrafunctional polyethylene glycol-co-polyglycolate copolymer ("4PEG2KG"):

30 grams of 4 arm polyethylene glycol, molecular weight 2000 ("4PEG2K") was dried at 100° C. for 16 hours prior to use. 30 grams 4PEG2K, 7.66 g of glycolide and 25 mg of stannous 2-ethylhexanoate were charged into a 3 necked flask equipped with a Teflon coated magnetic stirring needle. The flask was then immersed into silicone oil bath maintained at 160° C. The polymerization reaction was carried out for 16 h under nitrogen atmosphere. At the end of the reaction, the reaction mixture was dissolved in 100 ml toluene. The hydroxy terminated glycolate copolymer was isolated by pouring the toluene solution in 4000 ml cold hexane. It was further purified by repeated dissolution-precipitation process from toluene-hexane solvent-nonsolvent system and dried under vacuum at 60° C. It then was immediately used for end capping reaction mentioned below:

Part 2: Conversion of hydroxyl groups into carboxylic groups ("4PEG2KGS") and SNHS ester.

30 g of 4PEG2KG copolymer was dissolved in 150 ml dry pyridine. 8.72 g of succinic anhydride was added to it and the solution was refluxed for 2 h under nitrogen atmosphere. The polymer was isolated by pouring the cold pyridine solution to 4000 ml hexane. The acid terminated polymer ("4PEG2KGS") was used in SNHS activation reaction. Briefly, to a solution of 30 g of 4PEG2KGS in 300 ml dry methylene chloride were added 10.58 g of SNHS and 10.05 g DCC. The reaction mixture was stirred overnight under nitrogen atmosphere. Dicyclohexylurea was removed by filtration. The filtrate was evaporated and the residue obtained was redissolved in 100 ml toluene. The toluene solution was precipitated in 2000 ml hexane. The SNHS activated polymer was stored under nitrogen atmosphere until further use.

Example 5

Sulfonyl Chloride Activated Crosslinkers

Activation of tetrafunctional polyethylene glycol-co-polyglycolate copolymer ("4PEG2KGS") with tresyl chloride:

30 g of 4PEG2KG was dissolved in 10 ml dry benzene. The solution was cooled to 0° C. and 5.92 g of triethyl amine and 10.70 g tresyl chloride were added under nitrogen atmosphere. After refluxing for 3 h under nitrogen atmosphere, the reaction mixture was cooled and filtered to remove triethylamine hydrochloride. The filtrate was poured into 3000 ml hexane to precipitate the activated polymer. The residue was redissolved in THF and filtered over neutral alumina to remove traces of triethylamine hydrochloride. The polymer was recovered by adding the THF solution to 3000 ml diethyl ether and stored under nitrogen atmosphere.

Example 6

Synthesis of Multifunctional Oligopolycaprolactone Terminated with SNHS

Part 1: Synthesis of polycaprolactone ("PCL1"):

2.00 g of glycerol, 8.17 g of caprolactone and 50 mg of stannous 2-ethylhexanoate were charged into 100 ml Pyrex pressure sealing tube. The tube was frozen in liquid nitrogen and connected to vacuum line for 10 minutes. The tube then was connected to argon gas line and sealed under argon. The sealed reaction mixture then was immersed in oil bath maintained at 160° C. and polymerization was carried out for 16 h at 160° C. The polymer was recovered by dissolving it in 30 ml toluene and precipitating in 2000 ml cold hexane. The precipitated liquid oligomer was recovered and dried under vacuum for 1 day at 60° C.

Part 2: End-capping of PCL1 with succinic anhydride ("PCL-S"):

10 g of PCL1 was dissolved in 150 ml dry benzene. About 50 ml of benzene was distilled to remove traces of water from the reaction mixture. The solution was cooled to 30° C. To this warm solution, 6.67 g of triethyl amine and 7.86 g of succinic anhydride were added. The reaction mixture was then refluxed for 6 h and concentrated by distillation under vacuum. The product was recovered by adding the filtrate to 2000 ml cold dry hexane.

Part 3: Activation of PCL-S with SNHS:

PCL1-succinate (5.0 g) was dissolved in 10 ml of anhydrous methylene chloride, cooled to 0° C. and 7.82 g of N-hydroxysulfosuccinimide and 7.42 N,N-dicyclohexylcarbodiimide were added under stirring. After stirring the mixture overnight, the precipitated dicyclohexylurea was removed by filtration and the solution was concentrated by removing solvent. The $^1$H-NMR spectrum showed succinimide singlet at 2.80 ppm (2H).

Example 7

Preparation of Polyethylene Glycol-Co-Polytrimethylene Carbonate Copolymer Terminated with N-Hydroxysuccinimide Preparation of Tetrafunctional Polyethylene glycol-co-polytrimethylene carbonate copolymer ("4PEG10KTMC2"):

30 g of tetrahydroxy polyethylene glycol, molecular weight 10000, was dried under vacuum at 90-100° C. in a glass sealing tube. The tube then was cooled and transferred inside an air bag where 2.45 g of trimethylene carbonate and 20 mg of stannous octoate were added to the tube. The glass tube was then sealed under vacuum and heated with stirring at 155° C. and maintained at this temperature for 16 h. The polyethylene glycol-co-polytrimethylene carbonate polymer was cooled and recovered by breaking the glass sealing tube. It was further purified by several precipitations from toluene-hexane solvent-nonsolvent system.

Part 2: Synthesis of glutarate derivative of 4PEG10KTMC2 ("4PEG10KTMC2G"):

10 g of 4PEG10KTMC was dissolved in 120 ml dry toluene. About 50 ml of toluene was distilled to remove traces of water from the reaction mixture. The warm solution was cooled to 60° C. To this solution, 1.23 g of triethyl amine and 1.40 g of glutaric anhydride were added. The reaction mixture was heated to 60° C. for 1 h and filtered. The product was recovered by adding the filtrate to 2000 ml cold dry hexane.

Part 3: Activation of terminal carboxyl groups using N-hydroxysuccinimide ("4PEG10KTMC2GNHS"):

30 g of 4PEG10KTMC2G was dissolved in 100 ml of dry DMF and 1.53 g of N-hydroxysuccinimide and 5 g molecular sieves 3A° were added. 1.28 g of DCC dissolved in 5 ml dry DMF was added dropwise and the reaction mixture was kept at room temperature for 24 h under nitrogen atmosphere. The mixture was diluted with 50 ml cold benzene and precipitated using cold hexane. The precipitate was collected on a sintered glass filter with suction. The dissolution and precipitation procedure was then repeated three times, using toluene-diethyl ether as solvent-nonsolvent system and dried under vacuum. The product was stored under nitrogen atmosphere at −20° C. until further use.

Example 8

Succinated Polyhydroxy Compounds Activated with N-hydroxysulfosuccinimide ES 10 g of erythritol was dissolved in 200 ml dry toluene. About 50 ml of toluene was distilled to remove traces of water from the erythritol. The solution was cooled to 50-60° C. and 20 ml pyridine and 8.58 g of succinic anhydride were added to the solution. The reaction mixture was then refluxed for 3 h and unreacted pyridine and toluene were evaporated to dryness under reduced pressure. The residue was used in activation reaction.

Part 2: Activation of ES with SNHS:

Erythritol-succinate (ES, 2.0 g) was dissolved in 10 ml of anhydrous dimethyl formamide ("DMF"), cooled to 0° C. and 3.47 g of N-hydroxysulfosuccinimide and 3.30 N,N-dicyclohexylcarbodiimide were added under stirring. After stirring the mixture overnight, the precipitated dicyclohexylurea was removed by filtration and the solution was concentrated by removing solvent. It was further purified by column chromatography.

Example 9

Preparation of Synthetic Crosslinked Biodegradable Gels 1.57 g (0.8 mM) of 4 arm amine terminated polyethylene glycol molecular weight 2000 was dissolved in 10 ml 0.1 M sodium borate buffer at pH 9.5. 2 g of 4 arm SNHS activated 4PEG2KGS polymer (molecular weight 2500) was dissolved in phosphate buffered saline. These two solutions were mixed to produce a crosslinked gel. In another variation of this method, the 4PEG2KGS polymer solid was directly added to the amine terminated polymer solution to produce a crosslinked polymer.

In another variation, a crosslinker consisting of an equimolar solution of dilysine can be used in place of the 4 arm PEG amine solution to form a hydrogel. Gelation was seen to occur within 10 seconds of mixing the two solutions. Similarly, other crosslinkers described in examples 1 to 7 may be reacted in molar equivalent proportions with other amine terminated polymers such as albumin or amine terminated biodegradable polymers similar to described in Example 2. The preferred compositions for making biodegradable hydrogels were described in Table 2. The amine terminated polymer solution described above was added with 0.1% of F D and C blue or indigo dye prior to crosslinking reaction. The addition of dye allows the preparation of colored gels.

Example 10

Preparation of Composite Synthetic Crosslinked Colored Biodegradable Gels 3 grams of bovine serum albumin was dissolved in 3 ml of phosphate buffered solution. Commercial sutures based on synthetic biodegradable polymers, such as Vicryl was cut/ground into several small pieces (size less than 1 mm) using cryogenic grinding. These colored suture particles (approximately 100 mg) were mixed with the albumin solution to form a suspension. 100 mg of crosslinker such as 4PEG10KTMC2GNHS was mixed with 0.2 ml of albumin suspension. This viscous solution then was mixed with 40 mg of triethanol amine (buffering agent). The addition of triethanol amine gels the solution in 60 seconds. The colored suture particles entrapped in the crosslinked gel help to visualize the gel especially when under laparoscopic conditions and also acts to strengthen the hydrogel as a reinforcing agent. The suture particles in above examples can be replaced with biodegradable microparticles loaded with drugs or bioactive compounds.

Example 11

Formulation of SG-PEG with Di-lysine

A four arm PEG with SG end groups (Shearwater Polymers, approx. 9,100 g/mol, 0.704 grams, $6.5 \times 10^{-5}$ moles) was dissolved in 2.96 g 0.01 M pH 4.0 phosphate buffer (19.2% solids). Di-lysine (Sigma, 347.3 g/mol, 0.03 grams, $8.7 \times 10^{-5}$ moles) was dissolved in 3.64 grams of 0.1 M pH 9.5 borate buffer (0.8% solids). On combination of the two solutions, the percent solids was 10%. The di-lysine has 3 amine groups. The SG-PEG has 4 NHS groups. After correction for the less than 100% degree of substitution on the SG-PEG, the formulation gives a 1:1 stoichiometry of amine groups to NHS groups.

Example 12

Formulation of SG-PEG with Tri-lysine

A four arm PEG with SG end groups (Shearwater Polymers, approx. 9,100 g/mol, 0.675 grams, $6.2 \times 10^{-5}$ moles) was dissolved in 2.82 g 0.01 M pH 4.0 phosphate buffer (19.3% solids). Tri-lysine (Sigma, 402.5 g/mol, 0.025 grams, $6.2 \times 10^{-5}$ moles) was dissolved in 3.47 grams of 0.1 M pH 9.5 borate buffer (0.7% solids). On combination of the two solutions, the percent solids was 10%. The tri-lysine has 4 amine groups. The SG-PEG has 4 NHS groups. After correction for the less than 100% degree of substitution on the SG-PEG, the formulation gives a 1:1 stoichiometry of amine groups to NHS groups.

Example 13

Formulation of SG-PEG with Tetra-lysine

A four arm PEG with SG end groups (Shearwater Polymers, approx. 9,100 g/mol, 0.640 grams, $5.9 \times 10^{-5}$ moles)

was dissolved in 2.68 g 0.01 M pH 4.0 phosphate buffer (19.2% solids). Tetra-lysine (Sigma, 530.7 g/mol, 0.025 grams, 4.7×10$^{-5}$ moles) was dissolved in 3.30 grams of 0.1 M pH 9.5 borate buffer (0.8% solids). On combination of the two solutions, the percent solids was 10%. The tetra-lysine has 5 amine groups. The SG-PEG has 4 NHS groups. After correction for the less than 100% degree of substitution on the SG-PEG, the formulation gives a 1:1 stoichiometry of amine groups to NHS groups.

Example 14

Gel Time Measurement

Figure 11:
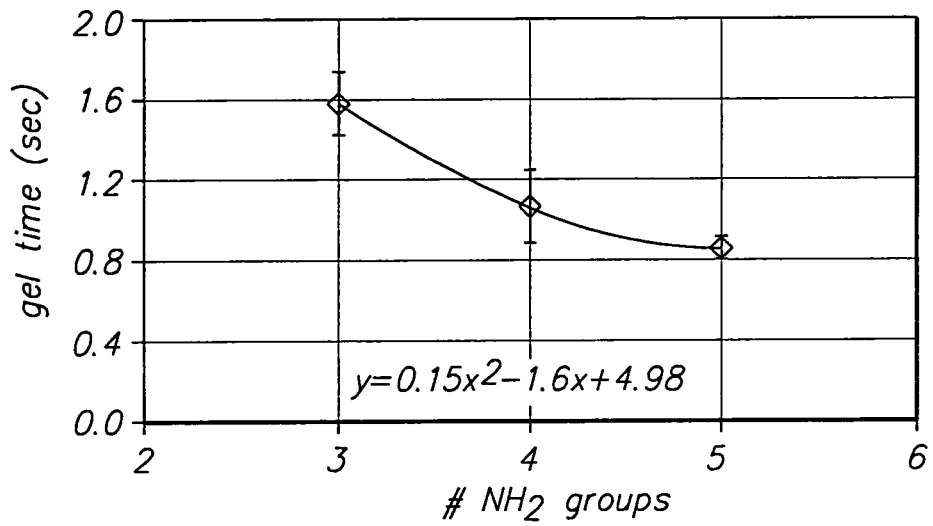
FIG. 11 shows the variation in gelation time with the number of amino groups for the reaction of 4 arm 10 kDa succinimidyl glutarate PEG ("SG-PEG") with di-, tri- or tetra-lysine.

The amine solution (100 µL) was aliquotted into a 100×13 test tube. A flea-stirbar (7×2 mm, Fisher Scientific p/n 58948-976) was placed in the test tube. The test tube was held stationary over a digital magnetic stirrer (VWR Series 400S Stirrer) set at 300 rpm. A 1 cc tuberculin syringe (Becton Dickinson, p/n BD309602) was filled with 100 µL of the ester solution. The syringe was inserted up to the flanges so that the distal end was just over the amine solution. Simultaneously the plunger was depressed and a stop watch started. When the solution solidifies sufficiently so that the stir bar stops spinning, the stop watch was stopped. Each solution was measured in triplicate and the mean±1 standard deviation was plotted. Results for the formulations of examples 1, 2 and 3 are shown in FIG. 11.

Example 15

Change in Gel Time as a Function of Ester Solution Age

Figure 12:
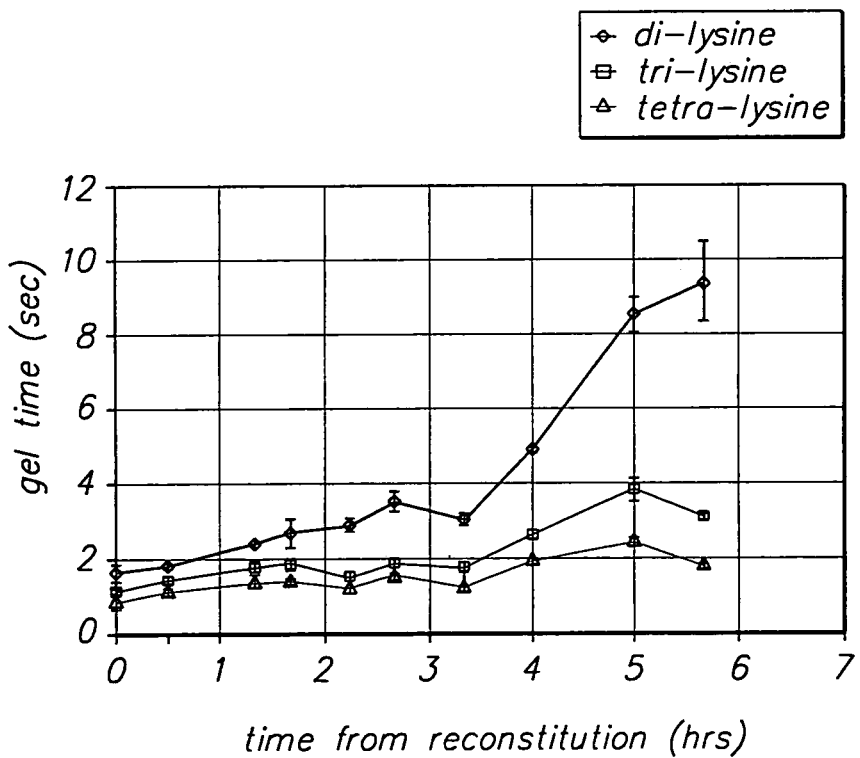
FIG. 12 shows the variation in gelation time with the solution age of the electrophilic functional polymer.

An important characteristic of these systems is the loss in reactivity over time from reconstitution of the ester solution. This loss in reactivity occurs due to hydrolysis of the N-hydroxysuccinimidyl ester, before the activated molecule can combine with its respective nucleophile. The loss of reactivity was characterized by measuring the change in gel time as a function of time from reconstitution of the NHS ester solution. The gel time was measured at ½ hour intervals. The NHS ester solution was stored at ambient conditions during this measurement. Results for the solutions described in Examples 11, 12 and 13 are shown in FIG. 12.

Example 16

Gel Formation at Different Percent Solids from 4 Arm CM-HBA-NS PEG and Lys-Lys

Using the gel time method described in Example 13, five different gel compositions were made using carboxymethyl hydroxybutyrate-hydroxysuccinimide end-capped 4 arm PEG (CM-HBA) (Shearwater Polymers) and di-lysine (Sigma). The formulations are listed below in Table 3.

TABLE 3

| Conc. (%) | CM-HBA (g) | Phosphate (g) | Lys-Lys (g) | Borate (g) |
|---|---|---|---|---|
| 8.5 | 0.2469 | 1.264 | 0.01 | 1.5012 |
| 10 | 0.2904 | 1.2209 | 0.012 | 1.4994 |
| 12.5 | 0.363 | 1.1483 | 0.015 | 1.4964 |
| 15 | 0.4356 | 1.0757 | 0.018 | 1.4936 |
| 20 | 0.5808 | 0.9305 | 0.024 | 1.4876 |

Figure 13:
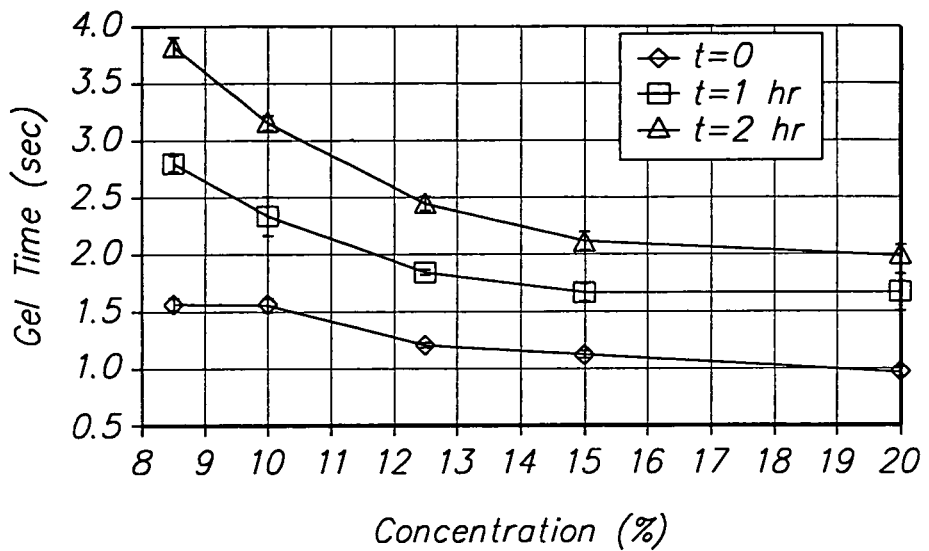
FIG. 13 shows the variation in gelation time with the concentration of biocompatible crosslinked polymer precursors, and with the solution age of the 4 arm 10 kDa carboxymethyl-hydroxybutyrate-N-hydroxysuccinimidyl PEG ("CM-HBA-NS") electrophilic functional polymer.

The formulations were adjusted to give a 1 to 1 ratio of electrophilic end groups on the CM-HBA (4) to nucleophilic reactive groups on the di-lysine ("Lys-Lys") (3). The CM-HBA quantities were dissolved in 0.01 M pH 5.0 phosphate buffer. The di-lysine was dissolved in 0.1 M pH 11 borate buffer. Gel time results are shown in FIG. 13. This data also shows that the higher percent solids solutions also are the most stable with respect to retention of speed of reaction.

Example 17

Degradation of Hydrogels

Figure 14:
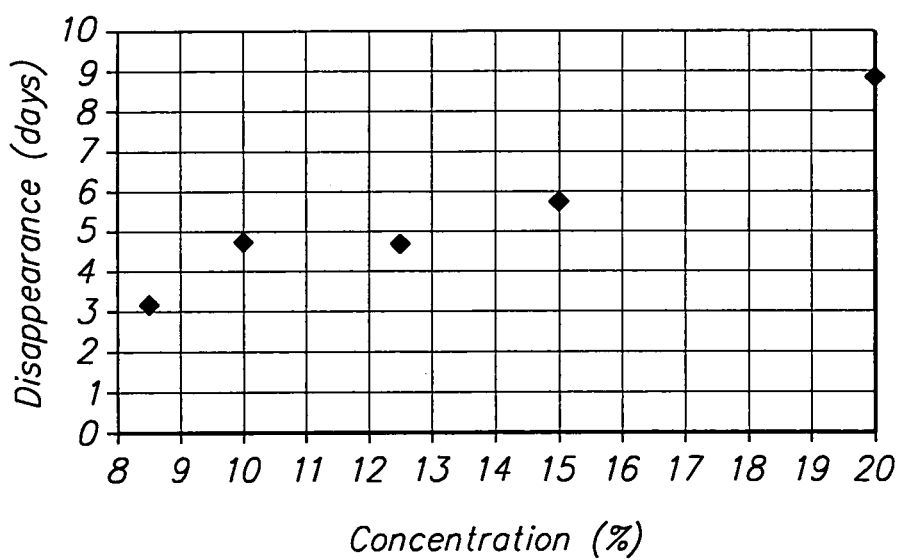
FIG. 14 shows the variation in degradation time with the concentration of biocompatible crosslinked polymer.

Hydrogel plugs made during the gel time measurements of Example 14 were placed in approximately 25 mL 0.1 M phosphate buffered saline at pH 7.4 in 50 mL Falcon tubes and placed in a constant temperature bath at 37° C. The hydrogel plugs were observed visually at periodic intervals and the time of gel disappearance noted. The data are plotted in FIG. 14.

Example 18

Precursor Spray Procedure to form a 7.5% Solids Hydrogel from 4 Arm SG and Dilysine An ethylene oxide sterilized air assisted sprayer was used in conjunction with aqueous solutions of polymerizable monomers. Solution 1 consisted of a 14.4% solution of 4 arm SG (MW 10,000 Da, purchased from Shearwater Polymers) dissolved in 0.01 M phosphate buffer at pH 4.0 and was sterile filtered (Pall Gelman syringe filter, p/n 4905) and drawn up in a sterile 5 cc syringe. Solution 2 consisted of a 1.2% solution of a dilysine (purchased from Sigma Chemicals) dissolved in 0.1 M borate buffer at pH 11 with 0.5 mg/mL methylene blue for visualization and was also sterile filtered and drawn up in a sterile 5 cc syringe. These solutions, when combined 1:1 on a volumetric basis, result in a 1:1 ratio of NHS ester to amine end group. The final % solids after combination is 7.5%. The two syringes were individually loaded in the two separate receptacles through a luer-lok type of linkage. Airflow from a regulated source of compressed air (an air compressor such as those commercially available for airbrushes) was connected to the device using a piece of Tygon tube. On compressing the syringe plungers a steady spray of the two liquid components was observed. When this spray was directed to a piece of tissue (rat cecum) a hydrogel coating was observed to form on the surface of the tissue. This hydrogel coating was rinsed with saline (the hydrogel coating is resistant to rinsing) and was observed to be well adherent to the tissue surface. Within a short period of time (less than a minute) an area of 10 cm×5 cm could be coated with ease.

Example 19

Precursor Spray Procedure to form a 12.5% Solids Hydrogel from 4 Arm CM and Dilysine A hydrogel barrier film made from 4 arm CM-HBA NS (MW 10,000 Da, purchased from Shearwater Polymers), and dilysine was similarly prepared and sprayed as described in Example 18. In the present example the 4 arm CM solution was made up to 24.0% solids and the dilysine solution was made up to 1.0% solids such that on combination in an equal volume delivery system a 1:1 ratio of NHS to amine end groups results, giving a final % solids of 12.5%.

Example 20

Spray Application of Crosslinker and Polymer to from Crosslinked Film

Two solutions (component A and component B) were prepared. Component A consisted of dilysine in 0.1 M borate buffer, pH 9.5. Component B consisted of either 4 arm SG-PEG or 4 arm CM-HBA-NS in 0.01 M phosphate buffer, pH 4.0. These solutions were prepared such that the amine to ester stoichiometric ratio was 1:1 and the final total solution concentration was 7.5% or 12.5%, respectively.

A Fibriject™ (Micromedics, Inc) 5 cc syringe holder and cap was used, preloaded with 5 cc of each solution and attached to a dual barrel atomizing sprayer. The sprayer has two hubs for the syringes to connect to allowing the two fluids to be advanced through two separate lumens over any preset distance. A third hub exists for the application of the atomizing gas. Air was used in this example. The distal tip of the sprayer contains a chamber where the gas expands out of an introduction tube, then flows past the two polymer solution nozzles in an annular space around each. The gas is accelerated in the annular spaces using a flow rate suitable for the complete atomization of the two fluid streams (~2 L/min.). Two overlapping spray cones are thus formed allowing for well mixed, thin, uniform coatings to be applied to surfaces.

Example 21

Adhesion Prevention in Rat Cecum Model

Surgical Procedure:

Male Sprague Dawley rats (250-350 grams,) were anesthetized with an intramuscular 4 ml/kg "cocktail" of Ketamine (25 mg/ml), Xylazine (1.3 mg/mL) and Acepromazine (0.33 mg/mL). The abdominal area was shaved and prepped for aseptic surgery. A midline incision was made to expose the abdominal contents. The cecum was identified and location within the abdomen was noted. The cecum was pulled out of the abdomen and the surface of one side was abraded using dry sterile gauze. A technique of abrading one area by stroking the surface 12 times with the gauze was used. The cecal arterial supply was interrupted using bipolar coagulation along the entire surface area of the damaged cecum.

The opposing abdominal sidewall which lays in proximity to the damaged cecal surface was deperitonealized with a scalpel blade and the underlying muscle layer was scraped to the point of hemorrhaging.

The cecum was sprayed with either the SG-PEG system or the CM-HBA-NS system using the air assisted spray method described in the preceding example. The cecum was placed with the damaged (ischemic area) side up opposite the damaged side wall. Active bleeding was controlled before closing. The peritoneum and muscle wall was closed with 3-0 nylon and the skin was closed with 4-0 silk. Rats were returned to their cages for one to two weeks at which time evaluation of the adhesion between the side wall and cecum was noted. The rats were killed at 10 days and the tenacity and extent of adhesion was evaluated. The results are summarized in Table 4.

TABLE 4

| Rat # | Material Applied | Reference Example | Findings on Day 10 |
|---|---|---|---|
| 403 | 7.5% 4aSG with Lys-Lys w/MB | Example 18 | Small amount of gel present on cecum. No adhesions from cecum to sidewall. No gel on sidewall. |
| 404 | 7.5% 4aSG with Lys-Lys w/MB | Example 18 | Some mesentary stuck to cecum. No gel. No adhesions. |
| 405 | 7.5% 4aSG with Lys-Lys w/MB | Example 18 | Small amount of gel present on cecum. Some mesentary stuck to cecum and sidewall. Some gel between mesentary and cecum where stuck. No adhesions. |
| 406 | 12.5% 4aCM with Lys-Lys w/MB | Example 19 | No gel present. No adhesions. |
| 407 | 12.5% 4aCM with Lys-Lys w/MB | Example 19 | No gel on cecum or sidewall. No adhesions. |
| 408 | 12.5% 4aCM with Lys-Lys w/MB | Example 19 | Rat died post-op (anesthesia overdose). |

While preferred illustrative embodiments of the invention are described above, it will be apparent to one skilled in the art that various changes and modifications may be made therein without departing from the invention, and it is intended in the appended claims to cover all such changes and modifications which fall within the true spirit and scope of the invention.

The invention claimed is:

1. A method of making a biocompatible degradable hydrogel to treat a medical condition of a patient comprising:
   identifying a medical condition for treatment by use of a hydrogel formed in situ in a patient and fully degradable in a patient in less than about 180 days; and
   mixing a first precursor with a second precursor in situ in the patient to form the hydro gel for treatment of the medical condition,
   with the first biocompatible synthetic hydrophilic polymer precursor having a water solubility of at least 1 gram per 100 milliliters and comprising at least two electrophilic functional groups; and the second biocompatible synthetic hydrophilic polymer precursor comprising at least two nucleophilic amine functional groups; and
   wherein
   (i) the first precursor is selected have only one or two chemically hydrolytically degradable ester bonds per every electrophilic functional group on the first precursor; and
   (ii) the second precursor comprises at least three nucleophilic functional groups;
   wherein the biodegradable groups of the hydrogel consist of the esters and the hydrogel as placed in situ in the patient is essentially fully degradable in a patient in less than about 180 days, and
   wherein mixing the first and the second synthetic hydrophilic polymer precursors forms crosslinking covalent bonds that are reaction products of the electrophilic and the nucleophilic groups, wherein essentially every ester bond in the hydrogel is separated from other ester bonds in the hydrogel by at least three covalent bonds when the hydrogel is formed.

2. The method of claim 1 wherein the medical condition is adhesion prevention.

3. The method of claim 1 wherein the medical condition is tissue adhesion.

4. The method of claim 1 wherein the medical condition is drug delivery.

5. The method of claim 1 wherein the medical condition is wound covering.

6. The method of claim 1 wherein the medical condition is tissue sealing.

7. The method of claim 1 wherein the medical condition is tissue coating.

8. The method of claim 1 wherein the solids concentration of the hydrogel ranges from 8.5% to 20% w/w.

9. The method of claim 1 wherein the second precursor has a molecular weight of less than about 1000 Daltons.

10. The method of claim 1 wherein the first precursor comprises carboxymethyl-hydroxybutyrate-N-hydroxysuccinimidyl polyethylene glycol.

11. The method of claim 1 wherein the first precursor comprises succinimidyl glutarate.

12. The method of claim 1 wherein the electrophilic functional groups of the first precursor comprise n-hydroxysuccinimide ester.

13. The method of claim 1 wherein the electrophilic functional groups of the first precursor comprise a member of the group consisting of carbonyldiimidazole, sulfonyl chloride, aryl halides, sulfosuccinimide ester, epoxide, aldehyde, maleimides and imidoester.

14. The method of claim 1 wherein the second precursor consists essentially of a member of the group consisting of dilysine, trilysine, and tetralysine.

15. The method of claim 1 wherein at least one of the precursors is selected to further comprise a chemical group having the formula $(CH_2CH_2O)_n$.

16. The method of claim 1 wherein the second precursor comprises a lysine.

17. The method of claim 1 wherein the hydrogel is essentially fully degradable in a patient in less than about 90 days.

18. The method of claim 1 wherein the hydrogel is essentially fully degradable in a patient in less than about 45 days.

* * * * *